United States Patent [19]
Coffindaffer et al.

[11] Patent Number: 5,807,545
[45] Date of Patent: Sep. 15, 1998

[54] COSMETIC COMPOSITIONS CONTAINING HYDROPHOBICALLY MODIFIED NONIONIC POLYMER AND UNSATURATED QUATERNARY AMMONIUM SURFACTANT

[75] Inventors: Timothy Woodrow Coffindaffer, Loveland; Melissa Smith Monich, Cincinnati; Steven Hilary Leitch, Fairfield; Raymond Edward Bolich, Jr., Maineville, all of Ohio; Patrick Columkille McCall, Iowa City, Iowa; Jose Antonio Carballada, Cincinnati, Ohio

[73] Assignee: The Procter & Gamble Co., Cincinnati, Ohio

[21] Appl. No.: 479,934

[22] Filed: Jun. 7, 1995

Related U.S. Application Data

[60] Division of Ser. No. 113,454, Aug. 27, 1993, which is a continuation-in-part of Ser. No. 111,762, Aug. 25, 1993, abandoned, which is a continuation of Ser. No. 776,960, Oct. 15, 1991, abandoned, which is a continuation-in-part of Ser. No. 671,576, Mar. 19, 1991, abandoned.

[51] Int. Cl.$^6$ ............................................. A61K 7/06
[52] U.S. Cl. .................. 424/70.11; 424/401; 424/70.19; 424/70.21; 424/70.28; 424/78.08; 424/47; 424/DIG. 1; 424/DIG. 2; 424/78.02; 424/70.12; 528/30
[58] Field of Search ................................ 424/78.02, 78.08, 424/DIG. 1, DIG. 2, 401, 70.11, 70.19, 70.21, 70.28, 45, 70.12, 47; 528/30

[56] References Cited

U.S. PATENT DOCUMENTS

| | | | |
|---|---|---|---|
| 3,395,041 | 7/1968 | Hsiung | 132/203 |
| 3,579,632 | 5/1971 | Sonnen | 424/70.1 |
| 3,723,325 | 3/1973 | Parran | 510/382 |
| 3,986,825 | 10/1976 | Sokol | 8/406 |
| 4,187,289 | 2/1980 | Eckhardt | 424/70.19 |
| 4,228,277 | 10/1980 | Landoll | 536/90 |
| 4,243,802 | 1/1981 | Landoll | 536/91 |
| 4,298,728 | 11/1981 | Majewicz et al. | 536/96 |
| 4,299,817 | 11/1981 | Hannan, III et al. | 424/70.13 |
| 4,331,167 | 5/1982 | Wajaroff | 132/203 |
| 4,336,246 | 6/1982 | Leon-Pekarek | 424/70.6 |
| 4,352,916 | 10/1982 | Landoll | 526/200 |
| 4,374,825 | 2/1983 | Bolich, Jr. et al. | 424/70.12 |
| 4,415,701 | 11/1983 | Bauer | 524/612 |
| 4,421,740 | 12/1983 | Burton | 424/70.13 |
| 4,426,485 | 1/1984 | Hoy et al. | 524/591 |
| 4,435,217 | 3/1984 | House | 106/181.1 |
| 4,445,521 | 5/1984 | Grollier et al. | 424/70.11 |
| 4,458,068 | 7/1984 | Warner et al. | 536/91 |
| 4,459,285 | 7/1984 | Grollier et al. | 424/74 |

(List continued on next page.)

FOREIGN PATENT DOCUMENTS

| | | |
|---|---|---|
| 0170927 | 2/1986 | European Pat. Off. |
| 0 408 311 | 1/1991 | European Pat. Off. |
| 412704 | 2/1991 | European Pat. Off. |
| 0 412 710 | 2/1992 | European Pat. Off. |
| 54043210 | 4/1979 | Japan. |
| 84007758 | 2/1984 | Japan. |
| 85023151 | 6/1985 | Japan. |
| 85026401 | 6/1985 | Japan. |
| 61053211 | 3/1986 | Japan. |
| 86023764 | 6/1986 | Japan. |
| 651151105 | 7/1986 | Japan. |
| 61186306 | 8/1986 | Japan. |
| 87195963 | 8/1987 | Japan. |
| 89-089881/12 | 10/1987 | Japan. |
| 62294606 | 12/1987 | Japan. |
| 2185269 | 7/1987 | United Kingdom. |

OTHER PUBLICATIONS

Advances in Chem. Series 0065-2392; 223, pp. 344-364, 1989.
Gleman, R.A., International Dissolving Pulp Conference, TAPPI, Feb. 1987, pp. 159-165.
Steiner, C.A., Polymer Prepr. (Am. Chem. Soc. Div. Polym. Chem.) 1985, pp. 224-225.
Chem. Abs. 103:27060b, Hercules Inc., Research Disclosure-252002, 1985 Publication.
Hercules Inc. Research Disclosure-252021, 1985.
Hercules Inc. Development Data-15 Publication, 1982.
Hercules Inc. Development Data-16 Publication, 1982.
Hercules Inc. Development Data-32 Publication, 1983.
Hercules Inc. Research Publication dated Nov. 2, 1984, entitled "Update WSP D-340 Performance in Surfactant Systems".
Cosmetics & Toiletries, vol. 103, March 1988, pp. 97–119.
Cosmetics & Toiletries, vol. 100, Mar. 1985, pp. 31–46.
Drug & Cosmetics Industry, pp. 2, 38-44, 102, Jun. 1984, pp. 38-44, 102.
M. S. Starch. (1984). Drug & Cosmetics Industry vol. 134, No. 6, pp. 38-40 and 102.
Oteri, R. et al. (1991). Cosmetics & Toiletries vol. 106, pp. 29-34.

*Primary Examiner*—Raj Bawa
*Attorney, Agent, or Firm*—Tara M. Rosnell; Loretta J. Henderson; Len W. Lewis

[57] ABSTRACT

Disclosed is a vehicle system having a thickening system which comprises a nonionic long-chain alkylated water-soluble polymer and a specific cationic quaternary ammonium surfactant component dispersed in a compatible solvent. The quaternary surfactant component has an iodine value of at least about 15. The quaternary surfactant component is characterized by having a sufficient level of unsaturated $C_{14}$–$C_{22}$ alkyl or $C_{14}$–$C_{22}$ alkyl amido $C_2$–$C_6$ alkylene radicals such that the average iodine value is at least about 15. These vehicle systems are useful in cosmetic compositions which are used to deliver an active component to the hair or skin. The vehicle systems are particularly useful in hair care compositions, especially rinse-off hair conditioning and styling compositions. In a particular rinse-off hair styling and conditioning composition hereof, the composition contains a vehicle system, as described above, and additionally contains a hair setting agent, a distributing aid, and a mono-long chain, tri-short chain quaternary ammonium surfactant.

32 Claims, No Drawings

U.S. PATENT DOCUMENTS

| | | | |
|---|---|---|---|
| 4,465,517 | 8/1984 | Shields | 106/35 |
| 4,485,089 | 11/1984 | Leipold | 424/49 |
| 4,496,708 | 1/1985 | Dehm et al. | 528/76 |
| 4,501,617 | 2/1985 | Desmarais | 524/5 |
| 4,523,010 | 6/1985 | Lukach et al. | 536/91 |
| 4,529,523 | 7/1985 | Landoll | 507/261 |
| 4,557,928 | 12/1985 | Glover | 514/345 |
| 4,581,230 | 4/1986 | Grollier et al. | 424/74 |
| 4,584,189 | 4/1986 | Leipold | 424/54 |
| 4,610,874 | 9/1986 | Matravers | 424/70.13 |
| 4,683,004 | 7/1987 | Goddard | 424/47 |
| 4,684,704 | 8/1987 | Craig | 526/200 |
| 4,707,189 | 11/1987 | Nickol | 106/173.01 |
| 4,719,099 | 1/1988 | Grollier et al. | 424/70.11 |
| 4,725,433 | 2/1988 | Natravers | 424/70.13 |
| 4,726,944 | 2/1988 | Osipow et al. | 510/120 |
| 4,788,006 | 11/1988 | Bolich, Jr. et al. | 510/121 |
| 4,826,970 | 5/1989 | Reid et al. | 536/66 |
| 4,834,968 | 5/1989 | Bolich | 424/47 |
| 4,883,536 | 11/1989 | Burdick | 106/162.82 |
| 4,894,224 | 1/1990 | Kuwata et al. | 514/781 |
| 4,902,499 | 2/1990 | Bolich, Jr. et al. | 424/70.12 |
| 4,954,335 | 9/1990 | Janchipraponvej | 424/70.28 |
| 4,954,341 | 9/1990 | Nakamura et al. | 424/70.19 |
| 4,963,348 | 10/1990 | Bolich, Jr. et al. | 424/70.12 |
| 4,981,902 | 1/1991 | Mitra et al. | 524/547 |
| 4,981,903 | 1/1991 | Garbe et al. | 524/547 |
| 4,988,506 | 1/1991 | Mitra et al. | 424/70.122 |
| 5,021,477 | 6/1991 | Garbe et al. | 424/70.12 |
| 5,034,218 | 7/1991 | Duvel | 424/70.12 |
| 5,061,481 | 10/1991 | Suzuki et al. | 424/63 |
| 5,078,990 | 1/1992 | Martin et al. | 510/124 |
| 5,094,838 | 3/1992 | Benson et al. | 424/47 |
| 5,100,657 | 3/1992 | Ansher-Jackson et al. | 424/70.12 |
| 5,100,658 | 3/1992 | Bolich, Jr. et al. | 424/70.12 |
| 5,104,646 | 4/1992 | Bolich, Jr. et al. | 424/70.13 |
| 5,120,531 | 6/1992 | Wells et al. | 424/70.15 |
| 5,126,126 | 6/1992 | Varaprath et al. | 424/70.121 |
| 5,277,899 | 1/1994 | McCall | 424/70.19 |

5,807,545

COSMETIC COMPOSITIONS CONTAINING HYDROPHOBICALLY MODIFIED NONIONIC POLYMER AND UNSATURATED QUATERNARY AMMONIUM SURFACTANT

This is a division of application Ser. No. 08/113,454, filed on Aug. 27, 1993, which is a continuation-in-part of application Ser. No. 08/111,762, filed on Aug. 25, 1993, abandoned which is a continuation of application Ser. No. 07/776,960, filed on Oct. 15, 1991, abandoned which is a continuation-in-part of application Ser. No. 07/671,576, filed on Mar. 19, 1991 abandoned.

TECHNICAL FIELD

The present invention relates to novel vehicle systems, and cosmetic compositions formulated therewith, based on nonionic long chain alkylated water-soluble polymer derivatives and unsaturated quaternary ammonium surfactants in a compatible diluent. A particularly useful application of the present invention is in hair care compositions, especially rinse-off hair conditioning and/or styling compositions.

BACKGROUND OF THE INVENTION

Typical hair conditioning products have a particular thick rheology that is desirable for such products. These products are based on the combination of a surfactant, which is generally a quaternary ammonium compound, and a fatty alcohol. This combination results in a gel-network structure which provides the composition with a thick rheology. However, while such compositions deliver conditioning benefits to the hair, such compositions also deposit on hair making hair look and feel dirty.

Alternative thickening systems have been used in hair care compositions, but none have been found to date which provide this same desirable rheology. Though hair care products thickened with polymer thickeners can be made to have a thick rheology, these products generally are characterized by an undesirable "slimy" feel and do not hold their poured shape.

Nonionic water-soluble cellulose ethers are employed in a variety of applications, including hair care compositions. Widely used, commercially-available nonionic cellulose ethers include methyl cellulose, hydroxy propyl methyl cellulose, hydroxyethyl cellulose, hydroxypropyl cellulose and ethyl hydroxyethyl cellulose.

Better thickening efficiency is realized with higher molecular weight cellulose ethers. However, production of such materials is difficult and expensive. Though crosslinking of these polymers is an alternative means to achieve high viscosity solutions, good crosslinking techniques are not known. Of course, high concentrations of polymers will also provide high viscosity but such an approach is inefficient and impractical, particularly due to the high expense involved. Furthermore, use of highly crosslinked polymers or high levels of polymeric thickeners may result in a vehicle system that is too elastic for the present uses.

Alternative water-soluble polymeric thickeners sometimes used to thicken hair care compositions are natural polysaccharides such as guar gum, xanthan gum and locust bean gum.

A number of references teach the use of nonionic cellulose ethers and water-soluble gums for thickening hair care compositions. See for example, U.S. Pat. No. 4,557,928, Glover, issued Dec. 10, 1985, teaching a hair conditioner comprising a suspension system which consists of one of glucan gum, guar gum, and hydroxyethylcellulose; and U.S. Pat. No. 4,581,230, Grollier et al., issued Apr. 8, 1986, which teaches cosmetic compositions for treating hair which comprise as thickening agents hydroxyethylcellulose, or water-soluble vegetable thickening agents, such as guar gum. Japanese Patent Publication 61-053211, published Mar. 7, 1986, discloses a hair colorant containing an aromatic alcohol, xanthan gum, and hydroxyethylcellulose.

Certain cellulose ethers have been disclosed in U.S. Pat. No. 4,228,277, Landoll, issued Oct. 14, 1980, which are relatively low molecular weight but which are capable of producing highly viscous aqueous solutions in practical concentrations. These materials are nonionic cellulose ethers having a sufficient degree of nonionic substitution selected from the group consisting of methyl, hydroxyethyl, and hydroxypropyl to cause them to be water-soluble and which are further substituted with a hydrocarbon radical having from about 10 to 24 carbon atoms in an amount between about 0.2 weight percent and the amount which renders said cellulose ether less than 1%, by weight, soluble in water. The cellulose ether to be modified is preferably one of low to medium molecular weight; i.e., less than about 800,000 and preferably between about 20,000 and 700,000 (about 75 to 2500 D.P.).

These modified cellulose ethers have been disclosed for use in a variety of composition types. Landoll ('277) teaches the use of these materials in shampoo formulations. Hercules trade literature teaches the use of these materials in shampoos, liquid soaps, and lotions. U.S. Pat. No. 4,683,004, Goddard, issued Jul. 28, 1987, discloses the use of these materials in mousse compositions for the hair. U.S. Pat. No. 4,485,089, Leipold, issued Nov. 27, 1984, teaches dentifrice compositions containing these materials.

These materials have now been found to provide a rheology very much like the desirable gel-network structure of typical hair conditioners (without the slimy feel associated with most polymeric thickeners), when they are combined with surfactants at certain critical levels. Such compositions are disclosed in U.S. Ser. Nos. 07/551,118, 07/551,119, and 07/551,120, all filed Jul. 16, 1990, by Bolich, Norton, and Russell.

Still, it remains desirable to provide further improved vehicle systems for use for cosmetic compositions. In particular, it is desirable to improve perceived spreadability of the compositions upon application by the user to the hair or skin. It is also desirable to provide improved wet feel of the hair on skin treated with such cosmetic compositions.

Hence, it is an object of the present invention to provide a vehicle system for a hair care and other cosmetic composition which provides a gel-network-like structure to the composition not based on a typical quaternary ammonium compound/fatty alcohol gel-network thickening system, which provides improved perceived spreadability upon application to the skin or hair and which provides improved wet feel of the hair or skin to the touch.

It is also an object of the present invention to provide a vehicle system, as described above, for a hair care and other cosmetic compositions which allows for dispersion of a wide variety of active hair or skin care components therein while providing improved wet feel and perceived spreadability relative to such compositions with prior disclosed vehicle systems.

In a particular aspect of this patent, it is an object to provide hair styling/conditioning compositions having excellent wet hair feel. Such compositions contain hair setting agents which typically should be accompanied by a distributing aid to facilitate spreading of the hair setting agent upon application to hair. The use of distributing aids, such as xanthan gum, unfortunately can negatively impact wet hair feel. Thus it is another object of this invention to provide a hair styling and conditioning composition containing a distributing aid for the hair setting agent that has excellent wet hair feel characteristics.

These and other objects will become readily apparent from the detailed description which follows.

SUMMARY OF THE INVENTION

The present invention relates to vehicle systems for use in cosmetic compositions which are polymer-based but which provide a rheology to the cosmetic compositions which mimics gel-network systems. These vehicle systems comprise a two component thickening system in a compatible diluent, wherein the primary thickener component is hydrophobically modified, nonionic, long chain alkoxylated polymer that is soluble in the diluent and the second thickener component is selected from quaternary ammonium surfactants having the formula, in salt form:

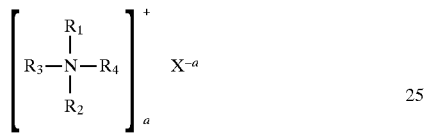

wherein X is a salt-forming anion, a is the ionic charge of X, the quaternary ammonium radicals $R_1$, $R_2$, $R_3$, and $R_4$ independently are $C_1-C_{22}$ alkyl, $C_{14}-C_{22}$ alkyl amido $C_2-C_6$ alkylene, or benzyl, and from two to three of said quaternary ammonium radicals, preferably two, are $C_{14}-C_{22}$ alkyl or $C_{14}-C_{22}$ alkyl amido $C_2-C_6$ alkylene (preferably $C_2-C_3$ alkylene), preferably $C_{16}-C_{22}$ alkyl, more preferably $C_{16}-C_{18}$ alkyl, or mixtures thereof, no more than two of said radicals are either $C_{14}-C_{22}$ alkyl amido $C_2-C_6$ alkylene or a combination of $C_{14}-C_{22}$ alkyl and $C_{14}-C_{22}$ alkyl amido $C_2-C_6$ alkylene, from one to two of said quaternary ammonium radicals, preferably two, are $C_1-C_6$ alkyl, preferably $C_1-C_3$ alkyl, more preferably methyl, and no more than one of said radicals is benzyl; or

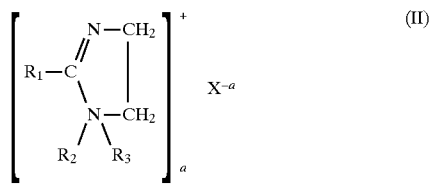

wherein X and a are as defined above, the radicals $R_1$, $R_2$, and $R_3$ independently are $C_1-C_{22}$ alkyl or benzyl, preferably $C_1-C_{22}$ alkyl, and two or three of said radicals are $C_{14}-C_{22}$ alkyls, preferably $C_{16}-C_{22}$ alkyl, or $C_{14}-C_{22}$ alkyl amido $C_2-C_6$ alkylene (preferably $C_2-C_3$ alkylene), or a mixture thereof, zero or one of said radicals are $C_1-C_6$ alkyl, preferably $C_1-C_3$ alkyl, more preferably methyl, zero or one of said radicals is benzyl; or a mixture of Formula I and II surfactants; wherein the quaternary ammonium surfactant component of the above description has a sufficient level unsaturation in the $C_{14}-C_{22}$ alkyl or $C_{14}-C_{22}$ alkyl amido $C_2-C_6$ alkylene radicals, or mixtures thereof, such that average iodine value of said component is at least about 15.

More specific embodiments of the cosmetic compositions of the present invention comprise:

(a) from about 80% to about 100%, preferably from about 80% to about 99.9%, of a vehicle system which comprises:

(A) from about 0.1% to about 10% by weight of the cosmetic composition of a hydrophobically modified nonionic water-soluble polymer which comprises a water-soluble polymer backbone and hydrophobic groups selected from the group consisting of $C_8-C_{22}$ alkyl, aryl alkyl, alkyl aryl groups and mixtures thereof; wherein the ratio of hydrophilic portion to hydrophobic portion of the polymer is from about 10:1 to about 1000:1; preferably the hydrophobically modified nonionic water-soluble polymer comprises a nonionic cellulose ether having a sufficient degree of nonionic substitution selected from the group consisting of methyl, hydroxyethyl, and hydroxypropyl to cause it to be water-soluble and being further substituted with a long chain alkyl radical having 10 to 24 carbon atoms in an amount between about 0.2 weight percent and the amount which renders said cellulose ether less than 0.2, preferably less than 1%, by weight soluble in water;

(B) from about 0.02% to about 5.0% by weight of the cosmetic composition of unsaturated quaternary ammonium surfactant as described above; and (C) from about 65% to about 99% by weight of the cosmetic composition of a compatible diluent, said nonionic water-soluble polymer being soluble in said diluent; and (b) from 0 to about 20%, preferably from about 0.1% to about 20%, of an additional active cosmetic component; wherein compositions comprising said vehicle system comprise no more than about 10% preferably no more than about 0.5%, of water-soluble surfactant materials (at 25° C.).

The unsaturated cationic quaternary ammonium surfactant as set forth above, can provide improved perceived spreading and improved wet feel of the hair or skin upon application by the user. These vehicle systems are particularly useful in hair care compositions especially rinse-off hair conditioners and styling/conditioners.

In another aspect of this invention, hair styling and conditioning compositions suitable for rinse-off application are provided with yet further improved wet hair feel. These compositions contain a two component thickening system in a compatible solvent as described above and a hair setting agent dispersed in the composition, a distributing aid for the hair setting agent, and additionally comprise as an essential ingredient a mono-long chain, tri-short chain cationic ammonium quaternary surfactant, or a mixture thereof, wherein the long chain is selected from $C_{14}-C_{22}$ alkyl or $C_{14}-C_{22}$ alkyl amido $C_2-C_6$ alkylene and the short chains independently are selected from the group consisting of $C_1-C_6$ alkyl and benzyl, with the number of benzyl radicals per molecule being zero or 1.

More specific embodiments of these hair styling and conditioning compositions comprise:

(a) from about 80% to about 99.5% of a vehicle system comprising:

(A) from about 0.1% to about 10.0% by weight of the cosmetic composition of a hydrophobically modified nonionic water-soluble polymer which comprises a water-soluble polymer backbone and hydrophobic groups selected from the group consisting of $C_8-C_{22}$ alkyl, aryl alkyl, alkyl aryl groups and mixtures thereof; wherein the ratio of the hydrophilic portion to the hydrophobic portion of the polymer is from about 10:1 to about 1000:1; and (B) from about 0.02% to about 10.0% by weight of the cosmetic composition of a unsaturated quaternary ammonium surfactant component of the formula:

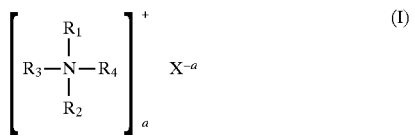

wherein X is a salt-forming anion, a is the ionic charge of X, the quaternary ammonium radicals $R_1$, $R_2$, $R_3$, and $R_4$ independently are $C_1$–$C_{22}$ alkyl, $C_{14}$–$C_{22}$ alkyl amido $C_2$–$C_6$ alkylene, or benzyl, and from two to three of said quaternary ammonium radicals, are $C_{14}$–$C_{22}$ alkyl or $C_{14}$–$C_{22}$ alkyl amido $C_2$–$C_6$ alkylene or mixtures thereof, no more than two of said radicals being $C_{14}$–$C_{22}$ alkyl amido $C_2$–$C_6$ alkylene or a combination of $C_{14}$–$C_{22}$ alkyl and $C_{14}$–$C_{22}$ alkyl amido $C_2$–$C_6$ alkylene, from one to two of said quaternary ammonium radicals are $C_1$–$C_6$ alkyls, and no more than one of said radicals is benzyl; or

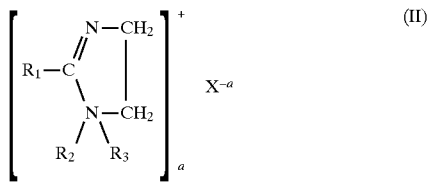

wherein X is a salt-forming anion, a is the ionic charge of X, radicals $R_1$, $R_2$, and $R_3$ independently are $C_1$–$C_{22}$ alkyl or benzyl, and two or three of said radicals are $C_{14}$–$C_{22}$ alkyl, or $C_{14}$–$C_{22}$ alkyl amido $C_2$ $C_6$ alkylene or a mixture thereof, zero or one of said radicals are $C_1$–$C_6$ alkyl, zero or one of said radicals is benzyl, or a mixture of Formula I and II surfactants; wherein said the quaternary ammonium surfactant component has a sufficient level of unsaturation in the $C_{14}$–$C_{22}$ alkyl or $C_{14}$–$C_{22}$ alkyl amido $C_2$–$C_6$ alkylene radicals, or mixture thereof, such that average iodine value of said component is at least 15; and (C) from about 65% to about 99% by weight of the cosmetic composition of a compatible diluent; and (b) from 0.05% to about 10%, by weight of the composition, of a hair setting agent;

(c) from about 0.01% to about 5% of a distributing aid; and (d) from about 0.05% to about 1.0%, by weight of the composition, of a mono-long chain, tri-short chain quaternary ammonium surfactant, or a mixture thereof of the formula:

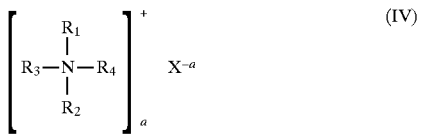

wherein X is a salt forming anion, a is the ionic charge of X, the quaternary ammonium radical $R_1$ is $C_{14}$–$C_{22}$ alkyl or $C_{14}$–$C_{22}$ alkyl amido $C_2$–$C_6$ alkylene, and quaternary ammonium radicals $R_2$, $R_3$, and $R_4$ independently are $C_1$–$C_6$ alkyl or benzyl, wherein zero or one of said $R_2$, $R_3$, and $R_4$ radicals is benzyl;
wherein said composition comprises no more than about 1.0% of water-soluble surfactants.

The compositions hereof comprise or, alternately, can consist essentially of or consist of the essential ingredients, as well as the optional ingredients, described herein.

DETAILED DESCRIPTION OF THE INVENTION

The essential as well as various optional components of the present compositions are described below. All solubilities are determined at 25° C., unless otherwise indicated. All percentages and ratios are by weight unless otherwise indicated. All percentages are by weight of the total composition, unless otherwise indicated.

HYDROPHOBICALLY MODIFIED WATER SOLUBLE POLYMER

The vehicle systems of the present invention contain, as an essential thickener component, a water soluble polymer. This thickening material is a hydrophobically modified nonionic water-soluble polymer. By "hydrophobically modified nonionic water-soluble polymer" is meant a nonionic water-soluble polymer which has been modified by the substitution with a sufficient amount of hydrophobic groups to make the polymer less soluble in water. Hence, the polymer backbone can be essentially any water-soluble polymer. For the compositions hereof, the unmodified polymer backbone should be sufficiently soluble such that forms a substantially clear solution when dissolved in water at a level of 1%, by weight of the solution, at 25° C. The hydrophobic groups can be $C_8$ to $C_{22}$ alkyl, aryl alkyl, alkyl aryl groups and mixtures thereof. The degree of hydrophobic substitution on the polymer backbone should be from about 0.10% to about 1.0%, by total weight of the polymer, preferably from about 0.4% to about 0.7%. More generally, the ratio of hydrophilic portion to hydrophobic portion of the polymer is from about 10:1 to about 1000:1.

A number of existing patents disclose nonionic polymer materials which meet the above requirements and which are useful in the present invention. U.S. Pat. No. 4,496,708, Dehm et al., issued Jan. 29, 1985, teaches water-soluble polyurethanes having hydrophilic polyether backbones and pendant monovalent hydrophobic groups to result in a hydrophilic/lipophilic balance of between about 14 and about 19.5. U.S. Pat. No. 4,426,485, Hoy et al., issued Jan. 17, 1984, discloses a water-soluble thermoplastic organic polymer having segments of bunched monovalent hydrophobic groups. U.S. Pat. No. 4,415,701, Bauer, issued Nov. 15, 1983, discloses copolymers containing a monoepoxide and a dioxolane.

The most preferred hydrophobically modified water soluble polymeric thickener materials for use in the present invention are disclosed in U.S. Pat. No. 4,228,277, Landoll, issued Oct. 14, 1980, which is incorporated herein by reference. The materials disclosed therein are thickeners comprising a nonionic long chain alkylated cellulose ether.

The cellulose ethers have a sufficient degree of nonionic substitution selected from the group consisting of methyl, hydroxyethyl and hydroxypropyl to cause them to be water-soluble. The cellulose ethers are further substituted with a hydrocarbon radical having about 10 to 24 carbon atoms in an amount between about 0.2 weight percent and the amount which renders said cellulose ether less than 0.2%, preferably less than 1%, by weight, soluble in water. The cellulose ether to be modified is preferably one of low to medium molecular weight, i.e., less than about 800,000 and preferably between about 20,000 and 700,000 (about 75 to 2500 D.P.).

The Landoll patent teaches that any nonionic water-soluble cellulose ether can be employed as the cellulose ether substrate. Thus, e.g., hydroxyethyl cellulose, hydroxypropyl cellulose, methyl cellulose, hydroxypropyl methyl cellulose, ethyl hydroxyethyl cellulose, and methyl hydroxyethyl cellulose can all be modified. The amount of nonionic substituent such as methyl, hydroxyethyl or hydroxypropyl is taught not to be critical so long as there is an amount sufficient to assure that the ether is water-soluble.

The preferred cellulose ether substrate is hydroxyethyl cellulose (HEC) of about 50,000 to 700,000 molecular weight. Hydroxyethyl cellulose of this molecular weight level is the most hydrophilic of the materials contemplated. It can thus be modified to a greater extent than can other water-soluble cellulose ether substrates before insolubility is achieved. Accordingly, control of the modification process and control of the properties of the modified product can be more precise with this substrate. Hydrophilicity of the most commonly used nonionic cellulose ethers varies in the general direction: hydroxyethyl→hydroxypropyl→hydroxypropyl methyl→methyl.

The long chain alkyl modifier can be attached to the cellulose ether substrate via an ether, ester or urethane linkage. The ether linkage is preferred.

Although the materials taught in Landoll are referred to as being "long chain alkyl group modified", it will be recognized that except in the case where modification is effected with an alkyl halide, the modifier is not a simple long chain alkyl group. The group is actually an alphahydroxyalkyl radical in the case of an epoxide, a urethane radical in the case of an isocyanate, or an acyl radical in the case of an acid or acyl chloride. Nonetheless, the terminology "long chain alkyl group" is used since the size and effect of the hydrocarbon portion of the modifying molecule completely obscure any noticeable effect from the connecting group. Properties are not significantly different from those of the product modified with the simple long chain alkyl group.

Methods for making these modified cellulose ethers are taught in Landoll ('277) at column 2, lines 36–65.

These materials have been found to be particularly desirable for use in the vehicle systems of the cosmetic compositions of the present invention. The materials are able to stabilize suspensions of dispersed phases, and when used with the additional components in the vehicle systems of the present invention, they produce rheologically thick products which lack the slimy feel characteristic of most polymeric thickeners.

One commercially available material which meets these requirements is NATROSOL PLUS Grade 330, a hydrophobically modified hydroxyethylcellulose available from Aqualon Company, Wilmington, Del. This material has a $C_{16}$ alkyl substitution of from about 0.4% to about 0.8% by weight. The hydroxyethyl molar substitution for this material is from about 3.0 to about 3.7. The average molecular weight for the water-soluble cellulose prior to modification is approximately 300,000. Another material of this type has a $C_{16}$ alkyl substitution of from about 0.40% to about 0.95%, by weight. The hydroxyethyl molar substitution for this material is from about 2.3 to about 3.3, and may be as high as about 3.7. The average molecular weight for the water soluble cellulose prior to modification is approximately 700,000.

The hydrophobically modified water soluble polymer thickener component is present in the cosmetic compositions of the present invention at from about 0.1% to about 10.0%, preferably from about 0.2% to about 5.0%.

UNSATURATED QUATERNARY AMMONIUM SURFACTANT

The present vehicle systems further comprise, as a second essential component, a second thickener which is an unsaturated water-insoluble, $C_{14}$–$C_{22}$ alkyl-substituted quaternary ammonium surfactant. By "water-insoluble surfactant" is meant surfactant materials which do not form clear isotropic solutions when dissolved in water at greater than 0.2 weight percent at 25° C. By "unsaturated" as applied to the $C_{14}$–$C_{22}$ alkyl substituted quaternary ammonium surfactant is meant quaternary ammonium surfactants having a sufficient amount of unsaturation such that it has an iodine value of at least about 15. Generally, the iodine value will be from about 20 to about 200. It should be understood that the iodine value is meant to describe the average level of unsaturation of the essential $C_{14}$–$C_{22}$ alkyl substituted quaternary ammonium surfactant. "Alkyl" as used herein, includes unsaturated radicals as well as saturated.

The essential $C_{14}$–$C_{22}$ alkyl-substituted quaternary ammonium surfactant component hereof constitutes materials of the formula, in salt form:

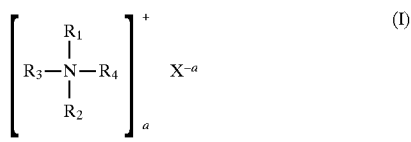

wherein X is a salt-forming anion, a is the ionic charge of X, the quaternary ammonium radicals $R_1$, $R_2$, $R_3$, and $R_4$ independently are $C_1$–$C_{22}$ alkyl, $C_{14}$–$C_{22}$ alkyl amido $C_2$–$C_6$ alkylene, or benzyl, and from two to three of said quaternary ammonium radicals, preferably two, are $C_{14}$–$C_{22}$ alkyl or $C_{14}$–$C_{22}$ alkyl amido $C_2$–$C_6$ alkylene (preferably $C_2$–$C_3$ alkylene), preferably $C_{14}$–$C_{22}$ alkyl, more preferably $C_{16}$–$C_{18}$ alkyl, or mixtures thereof, no more than two of said radicals are either $C_{14}$–$C_{22}$ alkyl amido $C_2$–$C_6$ alkylene or a combination of $C_{14}$–$C_{22}$ alkyl and $C_{14}$–$C_{22}$ alkyl amido $C_2$–$C_6$ alkylene, from one to two of said quaternary ammonium radicals, preferably two, are $C_1$–$C_6$ alkyls, preferably $C_1$–$C_3$ alkyl, more preferably methyl, and no more than one of said radicals is benzyl; or

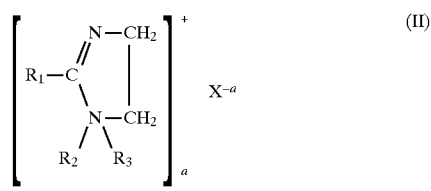

wherein X and a are as defined above, the radicals $R_1$, $R_2$, and $R_3$ independently are $C_1$–$C_{22}$ alkyl or benzyl, preferably $C_1$–$C_{22}$ alkyl, and two or three of said radicals, preferably two, are $C_{14}$–$C_{22}$ alkyl, preferably $C_{16}$–$C_{22}$ alkyl, or $C_{14}$–$C_{22}$ alkyl amido $C_2$–$C_6$ alkylene (preferably $C_2$–$C_3$ alkylene), or a mixture thereof, zero or one of said radicals are $C_1$–$C_6$ alkyl, preferably $C_1$–$C_3$ alkyl, more preferably methyl, zero or one of said radicals is benzyl, or a mixture of Formula I and II surfactants; wherein the quaternary ammonium surfactant component of the above description has a sufficient level unsaturation in the $C_{14}$–$C_{22}$ alkyl or $C_{14}$–$C_{22}$ alkyl amido $C_2$–$C_6$ alkylene radicals, or mixtures thereof, such that average iodine value of said component is at least about 15.

The anion X can be any salt-forming anion suitable for use in cosmetic compositions. Suitable anions include halogens (especially chloride and bromide), acetate, phosphate, nitrate, sulfate, and alkyl sulfate. Preferred anions generally are chloride, acetate, sulfate, and methyl sulfate.

Examples of unsaturated quaternary ammonium surfactants hereof include the salts of dimethyl di(unsaturated) tallow ammonium, dimethyl distearyl ammonium, dimethyl di(unsaturated)arachidyl ammonium, dioleyl dimethylammonium, di-rapeseed alkyl dimethyl ammonium, diricinoleyl dimethyl ammonium, and disoyadimonium, olealkonium.

Other examples include the salts of methyl-1-oleyl amido ethyl-2-oleyl imidazolinium, dierucyl dimethyl ammonium, and methyl-1-soya amido ethyl-2-soya imidazolinium.

It will be recognized by those skilled in the art that unsaturated quaternary ammonium surfactants, when purchased commercially, will normally also contain saturated quaternary ammonium surfactants of otherwise similar structure. An example of this is ADOGEN 470, commercially available from Sherex Chemical Company (Dublin, Ohio, U.S.A.), which contains a mixture of saturated and unsaturated ditallow dimethyl ammonium chloride. Compositions containing such materials are included within the scope of this invention as long as they contain the minimum level of surfactant defined herein having a level of unsaturation of surfactant falling within Formula (I) and (II) is sufficient such that the average iodine value is at least about 15.

This quaternary ammonium surfactant hereof is used at a level of from about 0.02% to about 10.0%, preferably from about 0.05% to about 3.0%, more preferably from about 0.05% to about 2.0%, by weight, of the composition.

Whereas the water insoluble unsaturated quaternary ammonium surfactant component hereof is referred to as a thickener material, it should also be recognized that it can also act as a conditioner for the hair and/or skin.

DILUENT

A third essential component in the vehicle systems of the present invention is a diluent which is a solvent for the hydrophobically modified water-soluble polymer and is compatible with the other components in the present compositions. Generally the diluent will comprise water or a water-lower alkanol (e.g., $C_2$–$C_4$ alcohols) mixture; preferably it will include at least about 25%, more preferably at least about 50%, even more preferably at least about 75%, by total weight of the diluent, of water. Rinse-off compositions, such as hair rinses, preferably utilize water as the diluent. The diluent is present in the compositions of the present invention at a level of from about 65% to about 99% by weight of the cosmetic composition.

The other vehicle components are dispersed or mixed in the diluent to provide an optimum thick rheology to cosmetic compositions formulated therewith which mimics the gel-network rheology of typical hair conditioning compositions. This rheology is characterized by a shear stress of from 0 to about 50 pascal, over a shear rate range of 0.04 $sec^{-1}$ to 25 $sec^{-1}$. The rheology is measured using a Bohlin Rheometer VOR with the following cone and plate set-up: cone has a 2.5 degree angle, plate is 30 mm in diameter, the gap between the truncated cone and plate is set at 70 $\mu$m, and the torque bar used is 20.148 g-cm. The sample amount is 0.35 ml and the sample is syringed onto the center of the plate. The system used is as follows: there is no initial delay time, the strain delay time is 25 sec, the integration time is 5 sec, the sensitivity is set at 1x, the shear sweep is up, the shear range is from about 0.0405 $sec^{-1}$ to 25.53 $sec^{-1}$ (shear No.=11 to 39), and the temperature is maintained constant between series at ambient temperature (20° C. to 25° C.).

ADDITIONAL THICHENER

The present vehicle systems can also comprise an additional thickening component, such as water-soluble polymeric materials other than the hydrophobically modified water soluble polymers described above. Examples of water-soluble polymers which may desirably be used as an additional thickening component in the present vehicle systems, are hydroxyethylcellulose, hydroxypropyl cellulose, hydroxypropyl methylcellulose, polyethylene glycol, polyacrylamide, polyacrylic acid, polyvinyl alcohol, polyvinyl pyrrolidone K-120, dextrans, for example Dextran purified crude Grade 2P, available from D&O Chemicals, carboxymethyl cellulose, plant exudates such as acacia, ghatti, and tragacanth, seaweed extracts such as sodium alginate, propylene glycol alginate and sodium carrageenan, and UCARE JR-polymer (a cationic modified hydroxyethyl cellulose available from Union Carbide). Preferred as the optional additional thickener for the present vehicle systems are natural polysaccharide materials. Examples of such materials are guar gum, locust bean gum, and xanthan gum. Also preferred as the additional thickener in the present compositions is hydroxyethyl cellulose having a molecular weight of about 700,000. It is preferred that these polymer materials not contain cellulose as this may interfere with obtaining optimum viscosities.

The additional thickening component, if present in the cosmetic compositions of the present invention, is preferably used at a level of from about 0.3% to about 5.0%, preferably from about 0.4% to about 3.0%.

DISTRIBUTING AID

An additional component in the vehicle systems of the present invention is a material which acts as a distributing aid for the composition. Such a material helps to distribute the cosmetic composition onto the hair or skin avoiding localized deposition of the active component onto the hair or skin. Without such a component in a composition, some active components in the composition would not be deposited and spread out as evenly, and hence, would not be quite as effective. In particular, a distributing aid is especially useful if ingredients that are tacky are included, such as hair setting polymers.

Distributing aid materials useful in the present invention are actually a subclass of the class of materials that can be used as the optional water-soluble polymer additional thickener in the present invention. This subclass is defined as follows: water-soluble polymer materials having high molecular weight, i.e., greater than 1,000,000; and/or strong ionic character. By strong ionic character is meant that the material conducts electricity at greater than 30 millivolts. This can be measured by evaluating conductance of a 1% solution of polymer in DRO (double reverse osmosis) water preserved with 0.03% Kathon CG (methylchloroisothiazolinone and methylisothiazolinone, a preservative available from Rohm & Haas) using a calibrated Corning 130 pH meter. The probes used were as follows: the reference electrode is an Orion Model 9001 single junction. The pH electrode is an Orion Model 9161, silver-silver chloride. The probes are set ⅜ of an inch apart. The pH meter is set to millivolt readings. The absolute measurement is recorded after 4 minutes immersion.

Examples of water soluble polymer materials which meet these requirements and hence, can act as distributing aids in the present compositions include xanthan gum; Dextran purified crude Grade 2P available from D&O chemicals; carboxymethyl celluloses; for example, CMC's 4H1F, 4M6F, 7HF, 7M8SF, 7LF, 9H4F, 9M8, 12M8P, 16M31, (all available from Aqualon); plant exudates such as acacia, ghatti and tragacanth; seaweed extracts such as sodium alginate, propylene glycol alginate, and sodium carrageenan; high molecular weight hydroxyethyl celluloses such as Natrosol 250H and Natrosol 250HHR (available from Aqualon); and pectin.

Because the class of materials which may act as distributing aids in the present invention is a subset of the optional water-soluble additional thickener, the materials in this subclass may be used to provide both benefits to the composition. For example, xanthan gum is a water-soluble natural polysaccharide material which additionally has a high molecular weight. Hence, this material could be used by itself to provide both additional thickening benefits and distributing benefits. However, it may be necessary to use such materials at slightly higher levels to provide both benefits.

It is also possible to use two separate materials as the optional water-soluble polymer additional thickener and the distributing aid of the present invention. This would be done when the water-soluble polymer additional thickener was not a high molecular weight material or of strong ionic character. Locust bean gum is such a material. A distributing aid such as xanthan gum could be used with locust bean gum to provide the additional distributing benefits.

If a distributing aid is present in the cosmetic compositions of the present invention, it should be present at a level of from about 0.02% to about 2.5%, preferably from about 0.05% to about 1.0%, of the cosmetic composition. If the distributing aid is bifunctional, i.e., acting as both the optional additional thickener and the distributing aid it should be present at a level of from about 0.2% to about 5% of the composition. Thus, in general, the distributing aid will be used at a level of about 0.02% to about 5%.

A distributing aid is particularly useful in hair care compositions of the present invention especially rinse-off hair conditioners. The distributing aid helps to spread some hair conditioning components, especially hair setting agents, evenly over the hair.

The present vehicle systems and cosmetic compositions formulated therewith should be substantially free of water-soluble surfactants. These materials are not compatible with the vehicle systems of the present composition. By "substantially free of water-soluble surfactants" is meant that the compositions comprise less than an amount of such surfactants that will destroy the present unique desirable rheology that is the object of the prevent invention. Generally, this will mean that the present compositions comprise no more than about 1%, preferably no more than about 0.5%, of such materials. Examples of specific water-soluble surfactant materials that can be particularly harmful to the present vehicle systems are alkyl sulfates and ethoxylated alkyl sulfates, such as ammonium lauryl sulfate; amphoteric surfactants which are derivatives of aliphatic secondary and tertiary amines; nonionic surfactants produced by the condensation of alkylene oxide groups with an organic hydrophilic compound, such as laureth-23 (sold under the trademark Brij 35 by ICI Americas); and high alkyl betaines, sulfo betaines, amido betaines and amido sulfobetaines, such as cetyl betaine.

The present vehicle systems and cosmetic compositions formulated therewith are also preferably substantially free of fatty alcohol materials, such as stearyl-, cetyl-, myristyl-, behenyl-, lauryl-, and oleyl alcohol. By "substantially free of fatty alcohol materials" is meant that the compositions of the present invention comprise no more than about 1% of these materials. These materials are commonly used in vehicle systems for hair conditioner products. However, these materials tend to deposit on the hair and leave the hair feeling dirty after use. These materials are not required in the present vehicle systems, as they are thickened with alternative materials which do not deposit on hair.

The present vehicle systems can be used in essentially any cosmetic products having a thick gel-network type rheology and which are used to deliver some active component onto the hair or skin. Such compositions would include skin moisturizing lotions, sunscreen compositions, and skin cleansing compositions. However, cosmetic compositions most desirably used with the present vehicle systems are hair care products, especially rinse-off hair care products where some active hair care component is to be deposited onto the hair but the vehicle carrying that component is desirably rinsed off of the hair with little or no deposition of the vehicle material onto the hair.

Generally, the present vehicle systems will not be useful in typical shampoo compositions since these compositions contain high levels of water-soluble surfactants, which as discussed supra, are incompatible with the present vehicle systems. However, the present vehicle systems are useful in typical hair coloring compositions, hair tonic or gel compositions, hair mousse compositions, and especially hair conditioning compositions.

ACTIVE COSMETIC COMPONENT

The cosmetic compositions of the present invention generally will comprise an additional active cosmetic component which provides some benefit to the hair or skin. The term "additional active component" is used since the unsaturated quaternary ammonium surfactant component hereof generally operates as a conditioner to hair or skin. Such materials may include moisturizing agents, sunscreen agents, cleaning agents (that are compatible with the present vehicle systems), and especially hair conditioning agents, hair styling agents, antidandruff agents, hair growth promoters, hair dyes and pigments, or perfumes.

A wide variety of conventional sunscreening agents are suitable for use in the cosmetic compositions of the present invention. Segarin, et al., at Chapter VIII, pages 189 et seq., of *Cosmetics Science and Technology*, disclose numerous suitable agents. Specific suitable sunscreening agents include, for example: p-aminobenzoic acid, its salts and its derivatives; anthranilates; salicylates; cinnamic acid derivatives; dihydroxycinnamic acid derivatives; trihydroxycinnamic acid derivatives; hydrocarbons; dibenzalacetone and benzalacetophenone; naphtholsulfonates; dihydroxynaphtholic acid and its salts; coumarin derivatives; diazoles; quinine salts; quinoline derivatives; hydroxy- or methoxy-substituted benzophenones; uric and vilouric acids; tannic acid and its derivatives; hydroquinone; and benzophenones.

Of these, 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl-4-[bis(hydroxypropyl)]-aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl p-dimethylaminobenzoate, 2-phenylbenzimidazole-5-sulfonic acid 2-(p-dimethyl-aminophenyl)-5-sulfonicbenzoxazoic acid, and mixtures of these compounds are particularly useful.

Examples of antidandruff aids suitable for use with the vehicle systems of the present invention include zinc pyrithione, sulphur, and selenium sulfide. One example of a hair growth promoter suitable for use with the vehicle systems of the present invention is Minoxidil, (6-amino-1, 2-dihydro-1-hydrpxy-2-imino-4-piperidino pyrimide) available from Upjohn. Hair oxidizing (bleaching) agents, such as hydrogen peroxide, perborate and persulfate salts, and hair reducing agents such as thioglycolates may also be used.

Additional Conditioners

Examples of conditioning materials suitable for use in the vehicle systems of the present invention are volatile liquid hydrocarbons. These are particularly useful for use in hair treatments.

These materials preferably have a boiling point in the range of about 99° C. to about 260° C. and have a solubility in water of less than about 0.1%. The hydrocarbons may be either straight or branched chain and may contain from about 10 to about 16, preferably from about 12 to about 16 carbon atoms. Examples of suitable hydrocarbons are decane, dodecane, tetradecane, tridecane and mixtures thereof.

Volatile silicones useful as an active conditioning component in the compositions of the present invention include silicone fluids such as cyclic and linear polydimethylsiloxanes. The number of silicon atoms in the cyclic silicones is preferably from about 3 to about 7, more preferably 4 or 5.

The general formula for the cyclic silicones is

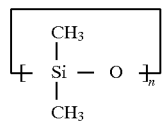

wherein n=3–7. The linear polydimethylsiloxanes have from about 3 to 9 silicon atoms and have the general formula:

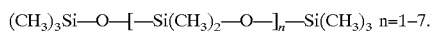

Silicones of the above type, both cyclic and linear, are available from Dow Corning Corporation, Dow Corning 344, 345 and 200 fluids; Union Carbide, Silicone 7202 and Silicone 7158; and Stauffer Chemical, SWS-03314.

The linear volatile silicones generally have viscosities of less than about 5 centipoise at 25° C. while the cyclic materials have viscosities less than about 10 centipoise at 25° C. A description of volatile silicones is found in Todd and Byers, "Volatile Silicone Fluids for Cosmetics", *Cosmetics and Toiletries*, Vol. 91, January 1976, pp. 27–32, incorporated herein by reference.

The volatile agent may be present in the compositions of this invention at a level of from about 1% to about 20%, preferably from about 2% to about 15%. The volatile silicones are the preferred volatile agents.

Nonvolatile silicone fluids are useful as the active hair conditioning component in the compositions of the present invention. They will generally have a viscosity in excess of 10 centipoise at 25° C. Examples of such materials include polydimethylsiloxanes (fluids and gums) aminosilicones and phenylsilicones. These include polyalkyl or polyaryl siloxanes with the following structure:

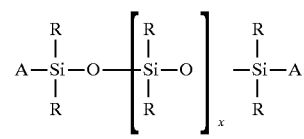

wherein R is alkyl or aryl, and x is an integer from about 7 to about 8,000 may be used. A represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair, are compatible with the other components of the composition, are chemically stable under normal use and storage conditions, and are capable of being deposited deposited on and of conditioning hair.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred.

Suitable methods for preparing these silicone materials are disclosed in U.S. Pat. Nos. 2,826,551 and 3,964,500 and references cited therein. Silicones useful in the present invention are also commercially available. Suitable examples include Viscasil, a trademark of the General Electric Company and silicones offered by Dow Corning Corporation and by SWS Silicones, a division of Stauffer Chemical Company.

Other useful silicone materials include materials of the formula:

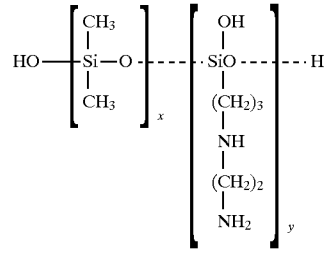

in which x and y are integers which depend on the molecular weight, the average molecular weight being approximately between 5,000 and 10,000. This polymer is also known as "amodimethicone".

Other silicone cationic polymers which can be used in the present composition correspond to the formula:

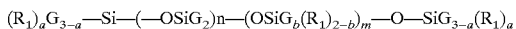

in which G is chosen from the group consisting of hydrogen, phenyl, OH, $C_1$–$C_8$ alkyl and preferably methyl; a denotes 0 or an integer from 1 to 3, and preferably equals 0;

b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10;

$R_1$ is a monovalent radical of formula $C_qH_{2q}L$ in which q is an integer from 2 to 8 and L is chosen from the groups

—N(R₂)CH₂—CH₂—N(R₂)₂
—N(R₂)₂
—N⁺(R₂)₃A⁻
—N⁺(R₂)₂CH₂—CH₂—N⁺(R₂)₃A⁻ in which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

These compounds are described in greater detail in European Patent Application EP 95,238. An especially preferred polymer corresponding to this formula is the polymer known as "trimethylsilylamodimethicone" of formula:

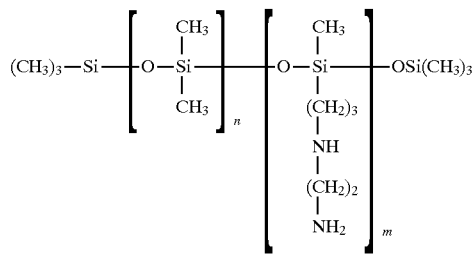

Compositions of the present invention including this material typically will comprise up to about 1.0% of the trimethylsilyl amodimethicone silicone conditioning material.

Other silicone cationic polymers may also be used in the present compositions, such as those of the formula:

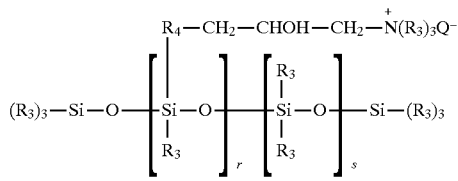

in which $R_3$ denotes a monovalent hydrocarbon radical having from 1 to 18 carbon atoms, and more especially an alkyl or alkenyl radical such as methyl;

$R_4$ denotes a hydrocarbon radical such as, preferably a $C_1$–$C_{18}$ alkylene radical or a $C_1$–$C_{18}$, and preferably $C_1$–$C_8$, alkyleneoxy radical;

$Q^-$ is a halide ion, preferably chloride;

r denotes an average statistical value from 2 to 20, preferably from 2 to 8;

s denotes an average statistical value from 20 to 200, and preferably from 20 to 50.

These compounds are described in greater detail in U.S. Pat. No. 4,185,017.

A polymer of this class which is especially preferred is that sold by UNION CARBIDE under the name "UCAR SILICONE ALE 56".

Silicone conditioning agents are used in the present compositions at levels of from about 0.1% to about 18%, preferably from about 0.5% to about 15%.

Preferred silicone conditioning agents for use in the present compositions comprise combinations of volatile silicone fluids having viscosities of less than about 10 centipoise, and from about 0.015% to about 9.0%, preferably from about 0.5% to about 2.0%, of silicone gums having viscosities of greater than about 1,000,000 centipoise, at ratios of volatile fluid to gum of from about 90:10 to about 10:90, preferably from about 85:15 to about 50:50.

Alternative preferable nonvolatile silicone materials for use in the present invention comprise non-volatile silicone fluids having viscosities of less that about 100,000 cP (centipoise) at 25° C., and from about 0.015% to about 9.0%, preferably from about 0.5% to about 2.0%, of silicone gums having viscosities greater than about 1,000,000 cP at 25° C., especially polydimethylsiloxane gums and polyphenylmethylsiloxane gums, at ratios of non-volatile fluid to gum of from about 70:30 to about 30:70, preferably from about 60:40 to about 40:60.

The efficacy of nonvolatile silicone hair conditioning agents can be enhanced through the use of silicone resin which is miscible with the silicone hair conditioning agent. Silicone resins are highly crosslinked polymeric siloxane systems. The crosslinking is introduced through the incorporation of trifunctional and tetrafunctional silanes with monofunctional or difunctional, or both, monomer units during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone resins will generally have at least about 1.1 oxygen atoms per silicon atom. Preferably, the ratio of oxygen:-silicon atoms is at least about 1.2:1.0. Typical silanes used in the manufacture of silicone resins are monomethyl-, dimethyl-, monophenyl-, diphenyl-, methylphenyl-, monovinyl-, and methyl-vinyl-chlorosilanes, and tetrachlorosilane. Preferred resins are the methyl substituted silicone resins, such as those offered by General Electric as GE SS4230 and SS4267. Commercially available silicone resins will generally be supplied in an unhardened form in a low viscosity volatile or nonvolatile silicone fluid. The silicone resins for use herein should be supplied and incorporated into the present compositions in such non-hardened form rather than as a hardened resin, as will be readily apparent to those skilled in the art.

The weight ratio of the nonvolatile silicone fluid conditioning component to the silicone resin component is preferably from about 4:1 to about 400:1. More preferably such ratio is from about 9:1 to about 200:1, most preferably from about 19:1 to about 100:1, particularly when the silicone fluid component is a polydimethylsiloxane fluid or a mixture of polydimethylsiloxane fluid and polydimethylsiloxane gum, as described above.

Other active hair care materials for use with the vehicle systems of the present invention are silicone polymer materials which provide both style retention and conditioning benefits to the hair. These include silicone polymers that are rigid silicone polymers. Such materials are described in U.S. Pat. No. 4,902,499, Bolich et al., issued Feb. 20, 1990, incorporated herein by reference.

Additional cationic conditioning materials may be used in the present compositions. In general, cationic surfactants useful as hair conditioning agents include both quaternary ammonium and amine cationic surfactant materials. If such a material other than the secondary thickener component is included in the present compositions it will generally be present at levels up to about 2.5%, preferably at from about 0.5% to about 2.0%, by weight of the composition.

Cationic surfactants that can be used, in general, contain amino or quaternary ammonium hydrophilic moieties which are positively charged when dissolved in the aqueous composition of the present invention. Cationic surfactants among those useful herein are disclosed in the following documents, all incorporated by reference herein: M. C. Publishing Co., *McCutcheon's. Detergents& Emulsifiers*, (North American Edition 1979); Schwartz, et al., *Surface Active Agents, Their Chemistry and Technology*, New York: Interscience Publishers, 1949; U.S. Pat. No. 3,155,591, Hilfer, issued Nov. 3, 1964; U.S. Pat. No. 3,929,678, Laughlin, et al., issued Dec. 30, 1975; U.S. Pat. No. 3,959,461, Bailey, et al., issued May 25, 1976; and U.S. Pat. No. 4,387,090, Bolich, Jr., issued Jun. 7, 1983.

Specific quaternary ammonium salts include dialkyldimethylammonium chlorides, wherein the alkyl groups have from about 12 to about 22 carbon atoms and are derived from long-chain fatty acids, such as hydrogenated tallow fatty acid (tallow fatty acids yield quaternary compounds wherein $R_1$ and $R_2$ have predominately from 16 to 18 carbon atoms). Examples of quaternary ammonium salts useful in the present invention include ditallowdimethyl ammonium chloride, ditallowdimethyl ammonium methyl sulfate, dihexadecyl dimethyl ammonium chloride, di(hydrogenated tallow)dimethyl ammonium chloride, dioctadecyl dimethyl ammonium chloride, dieicosyl dimethyl ammonium chloride, didocosyl dimethyl ammonium chloride, di(hydrogenated tallow)dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl)dimethyl ammonium chloride, and stearyl dimethyl benzyl ammonium chloride. Ditallow dimethyl ammonium chloride, dicetyl dimethyl ammonium chloride, and stearyl dimethyl benzyl ammonium chloride are commonly used quaternary ammonium salts.

Salts of primary, secondary and tertiary fatty amines are also preferred cationic surfactant materials for use herein. The alkyl groups of such amines preferably have from about 12 to about 22 carbon atoms, and may be substituted or unsubstituted. Secondary and tertiary amines are preferred, tertiary amines are particularly preferred. Such amines, useful herein, include stearamido propyl dimethyl amine, diethyl amino ethyl stearamide, dimethyl stearamine, dimethyl soyamine, soyamine, tri(decyl)amine, ethyl stearylamine, ethoxylated (2 moles E.O.) stearylamine, dihydroxyethyl stearylamine, and arachidylbehenylamine. Suitable amine salts include the halogen, acetate, phosphate, nitrate, citrate, lactate and alkyl sulfate salts. Such salts include stearylamine hydrochloride, soyamine chloride, stearylamine formate, N-tallowpropane diamine dichloride and stearamidopropyl dimethylamine citrate. Cationic amine surfactants included among those useful in the present invention are disclosed in U.S. Pat. No. 4,275,055, Nachtigal, et al., issued Jun. 23, 1981, incorporated by reference herein.

A particular category of cationic quaternary ammonium surfactants that can be advantageously incorporated into the present compositions in combination with the above-described essential unsaturated quaternary ammonium surfactants, are water-insoluble materials having the formula, in salt form:

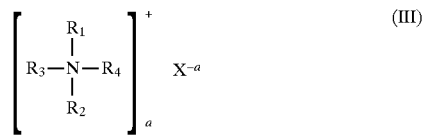

(III)

wherein X is a salt-forming anion as previously described, a is the charge of the anion X, the radicals $R_1$, $R_2$, $R_3$, and $R_4$ independently are $C_1$–$C_6$ alkyl, $C_{20}$–$C_{22}$ alkyl, or benzyl wherein one of said radicals is $C_{20}$–$C_{22}$ alkyl, preferably $C_{22}$, from two to three of said radicals are $C_1$–$C_6$ alkyl, preferably $C_1$–$C_3$, more preferably methyl, and zero or one of said radicals is benzyl.

The long chain alkyl (i.e. the $C_{20}$–$C_{22}$ alkyl) can be either saturated or unsaturated. If it is unsaturated, the surfactant may also fall within the scope of the essential unsaturated quaternary ammonium surfactant thickener described above. If that is the case, it should be included as part of the unsaturated quaternary ammonium surfactant thickener in any assessment of the compositions hereof.

A quaternary ammonium surfactant of Formula III particularly contemplated herein is: dimethyl behenyl benzyl ammonium salt (alternately referred to as behenalkonium salt), available from Witco Chemical Corp. (Memphis, Tenn., U.S.A.) as a chloride salt under the trade name KEMAMINE BQ-2802C. Another particularly contemplated Formula III material is dimethyl arachidyl benzyl ammonium salt.

The quaternary ammonium surfactant of Formula III is generally used at a level of from about 0.02% to about 10.0%, preferably from about 0.05% to about 3.0%, more preferably from about 0.05% to about 2.0%, by weight, of the composition.

Preferred combinations are compositions containing the surfactant of Formula III, especially in saturated form, in combination with the surfactants of Formulas I or II, or a mixture thereof, wherein the Formula I and II component comprises $C_{14}$–$C_{18}$ unsaturated alkyls, preferably at a weight ratio of (Formulas I and II):(Formula III) of about 1:1 to about 4:1.

A particularly useful combination of cationic surfactants that can be used comprises a mixture of di(unsaturated) $C_{16}$–$C_{18}$ alkyl (preferably tallow) dimethyl ammonium salt (e.g. the chloride salt as commercially available from Sherex Chemicals under the tradename ADOGEN 470)) and dimethyl (saturated or unsaturated behenyl and/or arachidyl, preferably saturated) benzyl ammonium salt (e.g. the chloride salt, at a weight ratio of about 1:1 at about 4:1, more preferably about 1:1 to about 3:1.

These combinations of cationic surfactants can provide improved overall performance for hair styling/conditioning products especially for as hair rinse products containing a styling/conditioning copolymer. Whereas the unsaturated quaternary ammonium surfactant thickener component, especially the preferred dimethyl, di($C_{16}$–$C_{18}$) alkyl-substituted surfactants, can provide products with excellent rheology, hair conditioning, and style hold, style hold can be improved through the use of the long chain $C_{20}$–$C_{22}$ alkyl-substituted materials of Formula III while retaining the excellent rheology and conditioning benefits of the unsaturated thickener component.

Hydrolyzed animal protein hair conditioning agents may also be included in the present compositions. Such materials are present in the compositions at levels of from about 0.1% to about 1.5%. An example of a commercially available material is sold under the tradename Crotein Q® from Croda, Inc.

Fatty alcohols are known hair conditioning agents and may be included in the present compositions. However, as described supra such materials tend to deposit on hair and leave hair feeling dirty after use. Hence, it may be described that any fatty alcohol materials included in the compositions of the present invention be present at levels no greater than about 1%.

Combinations of the aforementioned conditioning agents may also be used in the present compositions.

Hair Setting Aqent

The compositions of the present invention also can contain an effective amount of a hair setting agent to impart styling benefits upon application to hair. The term "hair setting agent" means a hair setting polymer and any carrier or diluent, not including the diluent of the vehicle system described above, that may be used in conjunction with the polymer. As used herein, "hair styling polymer" means any polymer, natural or synthetic, that can provide hair setting benefits. Polymers of this type are well known in the art. Generally, the level of hair styling polymer used will be at least about 0.05%, by weight, of the composition. Typically, it will be present at a level of from about 0.1% to about 10%, preferably from about 0.5% to about 8%.

The hair styling polymers hereof can be homopolymers, copolymers, terpolymers, etc. As used herein, the term "polymer" shall encompass all of such types of polymeric materials. For convenience in describing the polymers hereof, monomeric units present in the polymers may be referred to as the monomers from which they can be derived. The monomers can be ionic (e.g., anionic, cationic, amphoteric, zwitterionic) or nonionic.

Examples of anionic monomers include:
(i) unsaturated carboxylic acid monomers such as acrylic acid, methacrylic acid, maleic acid, maleic acid half ester, itaconic acid, fumaric acid, and crotonic acid;
(ii) half esters of an unsaturated polybasic acid anhydride such as succinic anhydride, phthalic anhydride or the like with a hydroxyl group-containing acrylate and/or methacrylate such as hydroxyethyl acrylate and, hydroxyethyl methacrylate, hydroxypropyl acrylate and the like;
(iii) monomers having a sulfonic acid group such as styrenesulfonic acid, sulfoethyl acrylate and methacrylate, and the like; and
(iv) monomers having a phosphoric acid group such as acid phosphooxyethyl acrylate and methacrylate, 3-chloro-2-acid phosphooxypropyl acrylate and methacrylate, and the like.

Examples of cationic monomers include:
(i) monomers derived from acrylic acid or methacrylic acid, which is referred to hereinafter collectively as (meth)acrylic acid, and a quaternarized epihalohydrin product of a trialkylamine having 1 to 5 carbon atoms in the alkyl such as (meth)acryloxypropyltrimethylammonium chloride and (meth)acryloxypropyl-triethylammonium bromide;
(ii) amine derivatives of (meth)acrylic acid or amine derivatives of (meth)acrylamide derived from (meth) acrylic acid or (meth)acrylamide and a dialkylalkanolamine having $C_1$–$C_4$ alkyl groups such as dimethylaminoethyl (meth)acrylate, diethylaminoethyl (meth) acrylate, dimethylaminopropyl (meth)acrylate, or dimethylaminopropyl (meth)acrylamide; and
(iii) derivatives of the products of the group (ii) above by (1) neutralization with an acid such as hydrochloric acid, or lactic acid, (2) modification with a halogenated alkyl, such as methyl chloride, ethyl chloride, methyl bromide, or ethyl iodide, (3) modification with a halogenated fatty acid ester such as ethyl monochloroacetate, or methyl monochloropropionate, and (4) modification with a dialkyl sulfate such as dimethyl sulfate, or diethyl sulfate.

Further cationic unsaturated monomers include amine derivatives of allyl compounds such as diallyldimethylammonium chloride and the like.

The cationic unsaturated monomers can be polymerized in cationic form. As an alternative, they can be polymerized in the form of their nonionic precursors, which are optionally modified to be cationic, for example, by a quaternizing agent (e.g. ethyl monochloroacetate, dimethyl sulfate, etc.).

Examples of the amphoteric monomers include zwitterionized derivatives of the aforementioned amine derivatives of (meth)acrylic acids or the amine derivatives of (meth) acrylamide such as dimethylaminoethyl (meth)acrylate, dimethylaminopropyl(meth)acrylamide by a halogenated fatty acid salt such as potassium monochloroacetate, sodium monobromopropionate, aminomethylpropanol salt of monochloroacetic acid, triethanolamine salts of monochloroacetic acid and the like; and amine derivatives of (meth) acrylic acid or (meth)acrylamide, as discussed above, modified with propanesultone.

These amphoteric monomers, like the aforementioned cationic monomers, can be polymerized in amphoteric form or, as an alternative, they can also be polymerized in the form of their precursors, which are then optionally converted into the amphoteric state.

Preferred ionic monomers include acrylic acid, methacrylic acid, dimethylaminoethyl methacrylate, quaternized dimethylaminoethyl methacrylate, maleic acid, maleic anhydride half esters, crotonic acid, itaconic acid, diallyldimethyl ammonium chloride, polar vinyl heterocyclics such as vinyl imidazole, vinyl pyridine, styrene sulfonate, and mixtures thereof. Especially preferred ionic monomers include acrylic acid, dimethylaminoethyl methacrylate, quaternized dimethylaminoethyl methacrylate, and mixtures thereof.

The hair setting polymers hereof will generally comprise from 0% to 100% ionic monomers and from 0% to 100% nonionic monomers, preferably from about 2% to about 75% ionic monomers and from about 25% to about 98% nonionic monomers, more preferably from about 5% to about 50% ionic monomers and from about 50% to about 95% nonionic monomers.

Representative examples of low polarity nonionic monomers are acrylic or methacrylic acid esters of $C_1$–$C_{24}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, and the like, the alcohols having from about 1–24 carbon atoms with the average number of carbon atoms preferably being from about 4–18, more preferably from about 4–12; styrene; chlorostyrene; vinyl esters such as vinyl acetate; vinyl chloride; vinylidene chloride; acrylonitrile; alpha-methylstyrene; t-butylstyrene; butadiene; cyclohexadiene; ethylene; propylene; vinyl toluene; alkoxyalkyl (meth)acrylate, such as methoxy ethyl (meth)acrylate, butoxyethyl (meth)acrylate; and mixtures thereof. Other nonionic monomers include acrylate and methacrylate derivatives such as allyl acrylate and methacrylate, cyclohexyl acrylate and methacrylate, and methacrylate, oleyl acrylate and methacrylate, benzyl acrylate and methacrylate, tetrahydrofurfuryl acrylate and methacrylate, ethylene glycol di-acrylate and -methacrylate, 1,3-butyleneglycol di-acrylate and -methacrylate, diacetonacrylamide, isobornyl (meth)acrylate, and the like.

Preferred nonionic monomers include n-butyl methacrylate, isobutyl methacrylate, 2-ethylhexyl methacrylate, methyl methacrylate, t-butylacrylate, t-butylmethacrylate, and mixtures thereof.

Representative polar nonionic monomers include acrylamide, N,N-dimethylacrylamide, methacrylamide, N-t- butyl acrylamide, methacrylonitrile, acrylate, and methacrylate alcohols (e.g. $C_2$–$C_6$ acrylate and methacrylate alcohols such as hydroxyethyl acrylate, hydroxyproxyl acrylate, hydroxyethyl methacrylate, and hydroxypropyl methacrylate), vinyl pyrrolidone, vinyl ethers, such as methyl vinyl ether, acyl lactones, vinyl pyridine, allyl alcohols, vinyl alcohols and vinyl caprolactam.

Examples of anionic hair styling polymers are copolymers of vinyl acetate and crotonic acid, terpolymers of vinyl acetate, crotonic acid and a vinyl ester of an alpha-branched saturated aliphatic monocarboxylic acid such as vinyl neodecanoate; and copolymers of methyl vinyl ether and maleic anhydride (molar ratio about 1:1) wherein such copolymers are 50% esterified with a saturated aliphatic alcohol containing from 1 to 4 carbon atoms such as ethanol or butanol; and acrylic copolymers and terpolymers containing acrylic acid or methacrylic acid as the anionic radical containing moiety such as copolymers with methacrylic acid, butyl acrylate, ethyl methacrylate, etc. Another example of an acrylic polymer which can be employed in the compositions of the present invention is a polymer of tertiary-butyl acrylamide, acrylic acid, and ethyl acrylate.

An example of an amphoteric polymer which can be used in the present invention is Octylacrylamide/Acrylates/Butylaminoethyl Methacrylate Copolymer, described generally in U.S. Pat. No. 4,192,861 as being a polymer of N-tert-octyl acrylamide, methyl methacrylate, hydroxypropyl methacrylate, acrylic acid and t-butyl aminoethyl methacrylate, of appropriate molecular weight for purposes hereof.

Examples of cationic hair styling polymers are copolymers of amino-functional acrylate monomers such as lower alkylamino alkyl acrylate or methacrylate monomers such as dimethyl aminoethylmethacrylate with compatible monomers such as N-vinylpyrrolidone or alkyl methacrylates such as methyl methacrylate and ethyl methacrylate and alkyl acrylates such as methyl acrylate and butyl acrylate. Cationic polymers containing N-vinylpyrrolidone are commercially available from GAF Corp.

Still other organic, hair styling polymers include carboxymethyl cellulose, copolymers of PVA and crotonic acid, copolymers of PVA and maleic anhydride, sodium polystyrene sulfonate, PVP/ethylmethacrylate/methacrylic acid terpolymer, vinyl acetate/crotonic acid/vinyl neodecanoate copolymer, octylacrylamide/acrylates copolymer, monoethyl ester of poly(methyl vinyl ether-maleic acid), and octylacrylamide/acrylate/butylaminoethyl methacrylate copolymers. Mixtures of polymers may also be used.

Highly preferred active hair care materials for use with the vehicle systems of the present invention are hair holding/styling polymers. Any of the silicone-containing hair styling polymers known in the art for this purpose can be used.

In its broadest sense, the silicone-containing polymers useful in the compositions of the present invention include all copolymers of silicone with a non-silicone adhesive polymer which: (a) when dried, the copolymer phase-separates into a discontinuous phase which includes the silicone portion and a continuous phase which includes the non-silicone portion; and (b) the silicone portion is covalently attached to the non-silicone portion. The silicone-containing polymers hereof are such that when formulated into the finished hair care composition, when dried, the polymer phase separates into a discontinuous phase which includes the polydimethylsiloxane macromer and a continuous phase which includes the backbone. The phase-separating nature of the compositions of the present invention may be determined as follows:

The polymer is cast as a solid film out of a good solvent (i.e., a solvent which dissolves both the backbone and the silicone). This film is then sectioned and examined by transmission electron micrography. Microphase separation is demonstrated by the observation of inclusions in the continuous phase. These inclusions should have the proper size to match the size of the silicone chain (typically a few hundred nm or less) and the proper density to match the amount of silicone present. This behavior is well documented in the literature for polymers with this structure (see, for example, S. D. Smith, Ph.D. Thesis, University of Virginia, 1987, and references cited therein).

A second method for determining phase-separating characteristics involves examining the enrichment of the concentration of silicone at the surface of a polymer film relative to the concentration in the bulk polymer. Since the silicone prefers the low energy air interface, it preferentially orients on the polymer surface. This produces a surface which is entirely covered by silicone even when the concentration of the silicone by weight in the whole polymer is low (2% to 20%). This is demonstrated experimentally by ESCA (electron spectroscopy for chemical analysis) of the dried film surface. Such an analysis shows a high level of silicone and a greatly reduced level of backbone polymer when the film surface is analyzed. (Surface here means the first few tens of Angstroms of film thickness.) By varying the angle of the interrogating beam the surface can be analyzed to varying depths.

The most preferred silicone-containing polymers comprise a vinyl polymeric backbone, preferably having a Tg or a Tm above about −20° C. and, grafted to the backbone, a polydimethylsiloxane macromer having a weight average molecular weight of from about 1,000 to about 50,000, preferably from about 5,000 to about 40,000, most preferably about 10,000 to about 20,000. As used herein, the abbreviation "Tg" refers to the glass transition temperature of the non-silicone backbone, and the abbreviation "Tm" refers to the crystalline melting point of the non-silicone backbone, if such a transition exists for a given polymer.

Highly preferred examples of such materials are the silicone-containing copolymers as described in the following patent applications: Ser. No. 07/758,319, Torgerson, Bolich and Garbe, filed Aug. 27, 1991; and Ser. No. 07/758,320, Bolich and Torgerson, filed Aug. 27, 1991; both of which are incorporated by reference herein, and in European Patent Application 90307528.1, Hayama et al. (Publication No. 0 408 311, Jan. 16, 1991). Such polymers typically have a weight average molecular weight of at least about 10,000, generally from about 75,000 to about 3,000,000, and also preferably, have a Tg of at least about −20 C.

In addition to the graft copolymers described above, useful copolymers include block copolymers containing up to about 50% (preferably from about 10% to about 20%) by weight of one or more polydimethyl siloxane blocks and one or more non-silicone blocks (preferably acrylates or vinyls).

Preferred polymers comprise a vinyl polymeric backbone having a Tg or a Tm above about −20° C. and, grafted to the backbone, a polydimethylsiloxane macromer having a weight average molecular weight of from about 1,000 to about 50,000, preferably from about 5,000 to about 40,000, most preferably about 20,000.

The silicone-containing polymers utilized as styling/conditioning agents generally comprise C monomers together with monomers selected from the group consisting of A monomers, B monomers, and mixtures thereof, as described in more detail below. These copolymers contain at least A or B monomers together with C monomers, and preferred copolymers contain A, B and C monomers.

Examples of useful copolymers and how they are made are described in detail in U.S. Pat. No. 4,693,935, Mazurek, issued Sep. 15, 1987, and U.S. Pat. No. 4,728,571, Clemens et al., issued Mar. 1, 1988, both of which reference. These herein by reference. These copolymers are comprised of monomers A, C and, optionally, B, which are defined as follows. A, when used, is at least one free radically polymerizable monomer or monomers. B, when used, comprises at least one monomer copolymerizable with A and is selected from the group consisting of polar (relative to A) monomers and macromers having a Tg or a Tm above about −20° C. When used, B may be up to about 98%, preferably up to about 80%, more preferably up to about 20%, of the total monomers in the copolymer. Polar monomers include ionic monomers as well as polar nonionic monomers. Monomer C comprises from about 0.01% to about 50.0% of the total monomers in the copolymer.

Representative examples of A monomers are acrylic or methacrylic acid esters of $C_1$–$C_{18}$ alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, and the like, the alcohols having from about 1–18 carbon atoms with the average number of carbon atoms being from about 4–12; styrene; vinyl acetate; vinyl chloride; vinylidene chloride; acrylonitrile; alpha-methylstyrene; t-butylstyrene; butadiene; cyclohexadiene; ethylene; propylene; vinyl toluene; and mixtures thereof. Preferred A monomers include n-butyl methacrylate, isobutyl methacrylate, 2-ethylhexyl methacrylate, methyl methacrylate, t-butylacrylate, t-butylmethacrylate, and mixtures thereof.

Representative examples of B monomers include acrylic acid, methacrylic acid, N,N-dimethylacrylamide, dimethylaminoethyl methacrylate, quaternized dimethylaminoethyl methacrylate, methacrylonitrile, polystyrene macromer, methacrylamide, maleic anhydride and its half esters, itaconic acid, acrylamide, acrylate alcohols, hydroxyethyl nethacrylate, diallyldimethyl ammonium chloride, vinyl pyrrolidone, vinyl ethers (such as methyl vinyl ether), maleimides, acylactones, vinyl pyridine, vinyl imidazole, other polar vinyl heterocyclics, styrene sulfonate, and mixtures thereof. Preferred B monomers include acrylic acid, N,N-dimethylacrylamide, dimethylaminoethyl methacrylate, quaternized dimethylaminoethyl methacrylate, vinyl pyrrolidone, and mixtures thereof. Additional suitable A and B monomers are described above in the discussion of non-silicone-containing polymers.

The C monomer has the general formula:

$$X(Y)_n Si(R)_{3-m} Z_m$$

wherein X is a vinyl group copolymerizable with the A and B monomers; Y is a divalent linking group; R is a hydrogen, lower alkyl, aryl or alkoxy; Z is a monovalent siloxane polymeric moiety having a number average molecular weight of at least about 500, is essentially unreactive under copolymerization conditions and is pendant from the vinyl polymeric backbone, described above; n is 0 or 1; and m is an integer from 1 to 3. C has a weight average molecular weight of from about 1,000 to about 50,000, preferably from about 5,000 to about 40,000, most preferably from about 10,000 to about 20,000. Preferably, the C monomer has the formula:

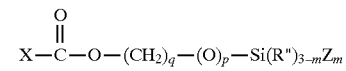

In those structures, m is 1, 2 or 3 (preferably m=1); p is 0 or 1; R″ is alkyl or hydrogen; q is an integer from 2 to 6; X is

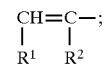

$R^1$ is hydrogen or —COOH (preferably $R^1$ is hydrogen); $R^2$ is hydrogen, methyl or —CH$_2$COOH (preferably $R^2$ is methyl); Z is

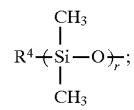

$R^4$ is alkyl, alkoxy, alkylamino, aryl, or hydroxyl (preferably $R^4$ is alkyl); and r is an integer from about 5 to about 700 (preferably r is about 130 to about 250). Particularly preferred is when p=0 and q=3.

The preferred polymers useful in the present invention generally comprise from 0% to about 98% (preferably from about 5% to about 98%, more preferably from about 50% to about 90%) of monomer A, from 0% to about 98% (preferably from about 7.5% to about 80%) of monomer B, and from about 0.1% to about 50% (preferably from about 0.5% to about 40%, most preferably from about 2% to about 25%) of monomer C. The combination of the A and B monomers preferably comprises from about 50.0% to about 99.9% (more preferably about 60% to about 99%, most preferably from about 75% to about 95%) of the polymer. The composition of any particular copolymer will help determine its formulational properties. For example, polymers which are soluble in an aqueous formulation preferably have the composition: from 0% to about 70% (preferably from about 5% to about 70%) monomer A, from about 30% to about 98% (preferably from about 3% to about 80%) monomer B, and from about 1% to about 40% monomer C. Polymers which are dispersible have the preferred composition: from 0% to about 70% (more preferably from about 5% to about 70%) monomer A, from about 20% to about 80% (more preferably from about 20% to about 60%) monomer B, and from about 1% to about 40% monomer C.

Polymers for use in the present invention include the following (the weight percents below refer to the amount of reactants added in the polymerization reaction, not necessarily the amount in the finished polymer):

acrylic acid/n-butylmethacrylate/polydimethylsiloxane (PDMS) macromer-20,000 molecular weight (e.g., 10/70/20 w/w/w) (I)

N,N-dimethylacrylamide/isobutyl methacrylate/PDMS macromer-20,000 molecular weight (e.g., 20/60/20 w/w/w) (II)

dimethylaminoethyl methacrylate/Isobutyl methacrylate/2ethylhexyl-methacrylate/PDMS macromer-20,000 molecular weight (e.g., 25/40/15/20 w/w/w/w) (III)

dimethylacrylamide/PDSM macromer-20,000 molecular weight (e.g., 80/20 w/w) (IV)

t-butylacrylate/t-butylmethacrylate/PDMS macromer-10,000 molecular weight (e.g., 56/24/20 w/w/w) (V)

t-butylacrylate/PDMS macromer-10,000 molecular weight (e.g., 80/20 w/w) (VI)

t-butylacrylate/N,N-dimethylacrylamide/PDMS macromer-10,000 molecular weight (e.g., 70/10/20 w/w/w) (VII)

t-butylacrylate/acrylic acid/PDMS macromer-10,000 molecular weight (e.g., 75/5/20 w/w/w) (VIII).

The polysiloxane-grafted polymers can be synthetized by free radical polymerization of the polysiloxane-containing monomers with the non-polysiloxane-containing monomers. The general principles of free radical polymerization methods are well understood. See, for example, Odian, "Principles of Polymerization," 2nd edition, John Wiley & Sons, 1981, pp. 179–318. The desired monomers are all placed in a reactor, along with a sufficient amount of a mutual solvent so that when the reaction is complete the viscosity of the reaction is reasonable. Typical monomer loadings are from about 20% to about 50%. Undesired terminators, especially oxygen, are removed as needed. This is done by evacuation or by purging with an inert gas, such as argon or nitrogen. The initiator is introduced and the reaction brought to the temperature needed for initiation to occur, assuming thermal initiators are used. Alternatively, redox or radiation initiation can be used. The polymerization is allowed to proceed as long as needed for a high level of conversion to be achieved, typically from a few hours to a few days. The solvent is then removed, usually by evaporation or by precipitating the polymer by addition of a nonsolvent. The polymer can be further purified, as desired.

The particle size of the hair setting agent of the present compositions may have some effect on performance in product. This, of course, will vary from polymer to polymer and from product to product.

The hair setting polymers are preferably provided in a solvent for the polymer, generally prior to combination with the vehicle systems of the present invention.

The solvent selected must be able to dissolve or disperse the particular hair styling polymer being used. Suitable solvents for use in the present invention, in general, include, but are not limited to, alkyl alcohols (such as linalool and decyl alcohol), hydrocarbons (such as isobutane, hexane, decane, dodecane, and tridecane), hydrocarbon esters (such as $C_8$–$C_{12}$ alkanoates, e.g. methyl decanoate, di($C_2$–$C_3$) alkyl adipates, e.g. diisopropyl adipate, $C_6$–$C_{10}$ alkyl acetates, e.g. octyl acetate, and benzoates, e.g. butyl benzoate,), volatile silicon derivatives, especially siloxanes (such as phenyl pentamethyl disiloxane, phenethyl pentamethyl disiloxane, methoxypropyl heptamethyl cyclotetrasiloxane, chloropropyl pentamethyl disiloxane, hydroxypropyl pentamethyl disiloxane, octamethyl cyclotetrasiloxane, decamethyl cyclopentasiloxane), ethers, such as di($C_5$–$C_7$)alkylethers, and mixtures thereof. Preferred solvents include volatile silicone fluids, and mixtures of silicone fluids with ester, ether, and or hydrocarbon solvents. The choice of solvent will depend upon the particular hair setting polymer chosen and the diluent utilized for the vehicle system, as described above. In general, it is preferred that the hair setting polymer solvent be dispersible, but immiscible, with the vehicle system diluent. Also, the hair setting polymer solvent is preferably volatile and not soluble in water. For purposes hereof, "volatile" means a boiling point, at atmospheric pressure, of less than about 300° C., preferably from about 100° C. to about 300° C., and "not soluble in water" means a water solubility in water at 25° C. of 0.2% or less, preferably about 0.1% or less, on a water plus solvent weight basis.

The performance of the styling polymers can be improved through the incorporation of a nonvolatile plasticizer into the styling polymer-solvent solution. The preferred solvents in these systems are volatile silicone fluids in which the styling polymer is soluble or dispersible. The plasticizer will generally be present in the compositions at a plasticizer: styling polymer weight ratio of about 1:20: to about 1:1, preferably from about 1:15 to about 1:2, more preferably from about 1:12 to about 1:2.5. As used herein, "nonvolatile" in regard to plasticizers means that the plasticizer exhibits essentially no vapor pressure at atmospheric pressure and 25° C. The polymer-volatile solvent solution should not suffer from substantial plasticizer weight loss while the volatile solvent is evaporating, since this would reduce plasticization of the styling polymer during use. The plasticizers for use herein should generally have boiling points of about 250° C. or higher. Such plasticizers are nonvolatile for purposes hereof.

The plasticizer should also be compatible with the hair styling polymer-volatile solvent solution. By "compatible" with respect to the plasticizer and the polymer-volatile solvent solution, it is meant that the plasticizer does not adversely interact with the hair styling/conditioning copolymer, and must be miscible in said solution. In general, the nonvolatile plasticizers for use herein will be of relatively low water solubility. The solubility parameter of these plasticizers will generally be between about 7 and about 10, preferably between about 8 and about 9 (units equal(cal/cc)$^{1/2}$). The solubility parameter is defined in the Polymer Handbook 3rd Ed. (John Wiley and Sons, New York), J. Brankrup and E. H. Immergut, Chapter VII, pp. 519–559, as the square root of the cohesive energy density and describes the attractive strength between molecules of the material. Solubility parameters may be determined by direct measurement, correlations with other physical properties, or indirect calculation as set forth by Immergut.

Plasticizers are well known in the art and are generally described in *Kirk-Othmer Encyclopedia of Chemical Technology*, second edition, Volume 15, pp. 720–789 (John Wiley & Sons, Inc. New York, 1968) under the topic heading "Plasticizers", and by J. Kern Sears and Joseph R. Darby in the text *The Technology of Plasticizers* (John Wiley & Sons, Inc., New York, 1982), both incorporated herein by reference. See especially in the Appendix of Sears/Darby Table A.9 at pages 983–1063 where a wide variety of plasticizers are disclosed.

The plasticizers for use herein include both cyclic and acyclic nonvolatile materials. Suitable categories of nonvolatile plasticizers include adipates, phthalates, isophthalates, azelates, stearates, citrates, trimellitates, silicone copolyols iso $C_{14}$–$C_{22}$ alcohols, methyl alkyl silicones, carbonates, sebacates, isobutgrates, oleates, phosphates, myristates, ricinoleates, pelargonates, valerates, oleates, camphor, and castor oil, and silicone copolyols.

Examples of adipate plasticizers include adipic acid derivatives such as diisobutyl adipate, bis(2-ethylhexyl) adipate, diisodecyl adipate, bis(2-butoxyethyl)adipate, and di-n-hexyl adipate.

Examples of phthalate plasticizers include phthalic acid derivatives such as dibutyl phthalate, butyl octyl phthalate, di-n-octyl phthalate, diisooctyl phthalate, bis(2-ethylhexyl) phthalate, n-octyl n-decyl phthalate, di-n-hexyl phthalate, isooctyl isodecyl phthalate, diisodecyl phthalate, ditridecyl phthalate, butyl cyclohexyl phthalate, diisoctyl benzyl phthalate, butyl benzyl phthalate, dicyclohexyl phthalate, diphenyl phthalate, isodecyl benzyl phthalate, and bis(2-butoxyethyl)phthalate.

Isophthalate plasticizers include bis(2-ethylhexyl) isophthalate, and diisooctyl benzyl phthalate.

Examples of azelate plasticizers include azelaic acid derivatives such as di(2-ethylhexyl)azelate, and bis(2-ethylhexyl)azelate.

Examples of stearate plasticizers include stearic acid derivatives such as n-butyl stearate, butyl acetoxystearate, and butoxyethyl stearate.

Examples of citrate plasticizers include citric acid derivatives such as acetyl tri-n-butyl citrate, tri-n-butyl citrate, and acetal tri-2-ethyl hexyl citrate.

Examples of trimellitate plasticizers include tri-(2-ethyl-hexyl)trimellitate, and triisooctyl trimellitate.

Other examples of plasticizers include dibutyl carbonate, butyl oleate, n-butyl, butyrate, isobutyl butyrate, isopropyl butyrate, dibutyl carbonate, ethyl palmitate, isooctyl palmitate, methyl ricinoleate, butyl ricinoleate, diisooctyl sebacate, triisobutyl phosphate, isodecy pelargonate, ethyl valerate, isocetyl alcohol, octododecanol, isopropyl myristate, isostearyl alcohol and methyl alkyl silicones having $C_2$–$C_{20}$ alkyl and from 1 to about 500 siloxane monomer units.

Silicone copolyols, described supra, can also be used as plasticizers.

If a plasticizer is used, the molecular weight, weight average, of the styling polymer is preferably at least about 200,000, more preferably from about 300,000 to about 800,000, most preferably from about 400,000 to about 600,000.

Other preferred cationic quaternary ammonium surfactants for inclusion in the compositions hereof, as a supplemental cationic conditioning agent, are mono-long chain, tri-short chain ammonium quaternary surfactants. Suitable surfactants of this category are those having the formula, in salt form:

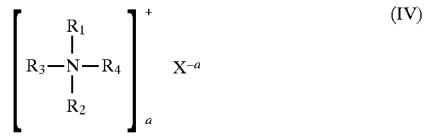

(IV)

wherein X is a salt-forming anion as previously described, a is the charge of the anion X, $R_1$ is a $C_{14}$–$C_{22}$ alkyl or $C_{14}$–$C_{22}$ alkyl amido $C_2$–$C_6$ alkylene, preferably $C_{16}$–$C_{22}$ alkyl, more preferably $C_{16}$–$C_{18}$ alkyl, and $R_2$, $R_3$, and $R_4$ independently are $C_1$–$C_6$ alkyl, or benzyl, preferably $C_1$–$C_3$ or benzyl, more preferably methyl or benzyl, wherein only one of the short chain radicals is benzyl. X is as previously described. The long chain radical can be either saturated or unsaturated. The Formula IV surfactant utilized preferably is more water-soluble than the quaternary surfactants of Formulas I and II that are present in the composition.

These cationic surfactants are particularly useful for improving wet feel of the compositions in formulations also containing a distributing aid. In particular, they are advantageously utilized in compositions containing hair styling agents, or other tacky materials, which require a distributing aid for adequate distribution of the hair setting agent or other tacky additive.

Preferred surfactants of Formula (IV) include (a) $C_{14}$–$C_{22}$ alkyl(saturated or unsaturated)dimethyl benzyl ammonium chlorides such as stearyl benzyl dimethyl ammonium chloride, or other salts thereof, and (b) $C_{14}$–$C_{22}$ alkyl (saturated or unsaturated)trimethyl ammonium chlorides, or other water soluble salts thereof. Preferred are $C_{14}$–$C_{22}$ unsaturated alkyl trimethyl ammonium chloride, commercially available in Adogen 471™ from Sherex Chemical Co. (Dublin, Ohio, U.S.A.). It is also contemplated to use combinations of (a) and (b), preferably with $C_{16}$–$C_{18}$ alkyl chains. Alternatively, other short chain alkyls can replace methyl (e.g. $C_2$–$C_6$ alkyls, preferably $C_2$–$C_3$) although methyl is preferred. The weight ratio of (a) to (b) is preferably from about 0.5:1 to 8:1, more preferably from about 1:1 to about 5:1, most preferably from about 1.5:1 to about 4:1.

Surfactants of the type described by Formula (IV) are generally used at a total level of from about 0.05% to about 1.0% by weight of the composition, preferably from about 0.1% to about 0.75%, more preferably from about 0.1% to about 0.4%. Also, preferably, the ratio of formula I plus II surfactants to Formula IV surfactants is from about 1:20 to about 20:1, more preferably from about 1:1 to about 15:1, more preferably from about 2:1 to about 10:1.

These additional active cosmetic materials are generally present at a total level of from about 0% to about 20%, preferably from about 0.1% to about 20%, by weight of the cosmetic composition. For purposes hereof, these additional active cosmetic components shall not include the unsaturated quaternary ammonium surfactants which are encompassed by Formulas I and II, even though such surfactants generally will have cosmetic efficacy, eg. as hair or skin conditioners. The 0% level reflects the situation when one of the vehicle component provides the hair care activity to the present compositions. For example, if the vehicle system comprises a water-insoluble quaternary ammonium compound, this material will provide hair conditioning benefits as well. The level of the active cosmetic care material varies depending upon which active material is chosen, the particular cosmetic compositions to be formulated therewith, and the level of benefit desired.

Other optional components that can be added to the cosmetic compositions of the present invention do not provide any direct cosmetic care benefit but instead enhance the composition in some way. Examples of such materials are coloring agents, such as any of the FD&C or D&C dyes; opacifiers, pearlescent aids, such as ethylene glycol distearate or TiO2 coated mica; pH modifiers, such as citric acid, succinic acid, phosphoric acid, sodium hydroxide, and sodium carbonate; perservatives, such as benzyl alcohol, ethyl paraben, propyl paraben, and imidazolidonyl urea; and antioxidants. Such agents generally are used individually at a level of from about 0.001% to about 10%, preferably from about 0.01% to about 5%, of the hair care composition. The vehicle systems and cosmetic compositions of the present invention can be made using conventional formulation and mixing techniques. In one procedure for manufacture, a silicone conditioner, quaternary ammonium surfactant, and at least a portion of the solvent component are premixed prior to the addition of the remaining components. Methods of making various types of cosmetic compositions are described more specifically in the following examples.

The following examples illustrate the present invention. It will be appreciated that other modifications of the present invention within the skill of those in the cosmetic composition formulation art can be undertaken without departing from the spirit and scope of this invention.

All parts, percentages, and ratios herein are by weight unless otherwise specified.

EXAMPLE I

The following is a hair styling rinse composition representative of the present invention.

| Component | Weight % |
|---|---|
| Styling Agent Premix | |
| Silicone Copolymer[1] | 2.00 |

-continued

| Component | Weight % |
|---|---|
| Phenylpentamethyl disiloxane | 9.00 |
| Xanthan Premix | |
| | |
| Xanthan gum | 0.25 |
| DRO $H_2O$ | 25.00 |
| Main Mix | |
| | |
| Dioleyl-dimethylammonium chloride (DODMAC) | 0.50 |
| EDTA, disodium salt | 0.10 |
| D.C. 929[2] | 2.00 |
| Perfume | 0.10 |
| Natrosol Plus CS Grade D-67[3] | 0.75 |
| Locust bean gum | 0.15 |
| Kathon CG[4] | 0.04 |
| DRO $H_2O$ | q.s. to 100% |

[1]20/60/20 N,N-dimethylacrylamide/isobutyl methacrylate/PDMS macromer (20,000 MW), polymer molecular weight about 300,000.
[2]Amodimethicone, commercially available from Dow Corning
[3]Hydrophobically modified hydroxethylcellulose having a $C_{16}$ alkyl substitution of from about 0.50% to about 0.95%, by weight, and a hydroxyethyl molar substitution of from about 2.3 to about 3.3, and where the average molecular weight of the hydroxyethyl cellulose prior to substitution is approximately 700,000, available from Aqualon Company.

The composition is prepared as follows. The DRO (double reverse osmosis) water is first heated to 71° F. The DODMAC, EDTA, and D.C. 929 are added to the water and mixed for about 5 minutes. The Natrosol is added to the composition with mixing. The Locust Bean Gum is added to the composition with mixing. The composition is then homogenized with a disperser, for example a Gifford-Wood mill, for about 2 minutes. The batch is then cooled to 38° F. The xanthan gum premix, styling agent premix, perfume and Kathan CG are added to the composition with mixing for about 10 minutes. The batch is cooled to ambient temperature and stored.

EXAMPLE II

The following is a hair styling rinse composition representative of the present invention.

| Component | Weight % |
|---|---|
| Styling Agent Premix | |
| | |
| Silicone Copolymer[1] | 3.00 |
| Phenylpentamethyl disiloxane | 9.00 |
| Hydroxypropylpentamethyl disiloxane | 6.00 |
| Silicone Gum Premix | |
| | |
| Silicone Gum G.E. SE 76[2] | 0.50 |
| Decamethyl cyclopentasiloxane | 4.00 |
| Main Mix | |
| | |
| Natrosol Plus CS Grade D-67[3] | 0.60 |
| Locust bean gum | 0.50 |
| EDTA, disodium salt | 0.15 |
| ADOGEN 470[5] | 0.65 |
| Glydant[4] | 0.40 |
| Perfume | 0.20 |
| DRO $H_2O$ | q.s. to 100% |

[1]10/70/20 acrylic acid/n-butyl methacrylate/silicone macromer, the macromer having a molecular weight of about 20,000, prepared in a manner similar to Example C-2c of U.S. Pat. No. 4,728,571, Clemens, issued March 1, 1988, polymer molecular weight about 300,000
[2]Commercially available from General Electric
[3]hydrophobically-modified hydroxyethyl cellulose commercially available from Aqualon Co.
[4]preservative commercially available from Glyco, Inc.
[5]Partially hydrogenated ditallow dimethyl ammonium chloride, commercially available from Sherex Chemical Company, Dublin, Ohio, USA.

The composition is prepared as follows. The DRO water is heated to 71° F. The ADOGEN 470, EDTA, and silicone gum premix are added to the water with mixing for about 5 minutes. The Natrosol is added with mixing. The Locust Bean Gum is added with mixing. The composition is then homogenized with a disperser, for example a Gifford-Wood mill, for about 2 minutes. The batch is cooled to 38° F. and the styling agent premix, the perfume and the Glydant are added with mixing for about 10 minutes. The batch is cooled to ambient temperature and stored.

EXAMPLE III

The following is a hair styling rinse composition representative of the present invention.

| Component | Weight % |
|---|---|
| Natrosol Plus CS Grade D-67[1] | 1.20 |
| Xanthan Gum | 0.25 |
| Citric Acid | 0.073 |
| Sodium Citrate | 0.175 |
| Kathon CG | 0.033 |
| ADOGEN 470[3] | 0.75 |
| Hydrogenated Tallow Betaine | 0.33 |
| Styling Agent Premix | |
| | |
| T-Butyl Acrylate/PDMS Copolymer (10,000 MW - 80/20 W/W) | 2.50 |
| Phenethyl Pentamethyl Disiloxane | 1.875 |
| D4 Cyclomethicone | 5.625 |
| Silicone Premix | |
| | |
| Polydimethyl Siloxane Gum/ D5 Cyclomethicone (15/85)[2] | 2.333 |
| Perfume | q.s. |
| DRO Water | q.s. to 100% |

[1]Hydrophobically modified hydroxyethyl cellulose available from Aqualon Corp.
[2]G.E. SE-76 gum available from G.E. Silicones
[3]Partially hydrogenated ditallow dimethyl ammonium chloride, commercially available from Sherex Chemical Company, Dublin, Ohio, USA The composition is prepared as follows. The xanthan gum is first slurried in water at 4% xanthan gum, until fully hydrated. In a separate vessel the copolymer is mixed into the phenethyl pentamethyl disiloxane and D4 cyclomethicone.

The remaining water is preheated to about 71° C. The ADOGEN 470, citric acid, sodium citrate, and hydrogenated tallow betaine are added to the water and mixed until melted. This mixture is then cooled to about 65° C. The Natrosol Plus, silicone gum premix, Kathon and perfume are added and mixed until homogeneous. This mixture is then cooled to about 38° C. The xanthan gum premix and copolymer premix are then added and the mixture is agitated until homogeneous. The resulting composition is cooled to ambient temperature.

EXAMPLE IV

The following is a hair conditioning rinse composition which is representative of the present invention.

| Component | Wt. % |
|---|---|
| Silicone Gum Premix | |
| Octamethyl Cyclotetrasiloxane | 3.00 |
| G.E. SE 76[2] | 0.50 |
| Main Mix | |
| Natrosol Plus CS Grade D-67[1] | 1.25 |
| Di rapeseed alkyl dimethyl ammonium chloride (DRaDMAC) | 0.75 |
| Stearamide DEA | 0.10 |
| Kathon CG | 0.04 |
| DRO Water and fragrance | q.s. to 100% |

[1]Hydrophobically modified hydroxethylcellulose available from Aqualon
[2]Silicone gum available from General Electric The composition is prepared as follows. The DRO water is first heated to 71° C. The DRaDMAC, stearamide DEA, Natrosol, and the Silicone gum premix are added with mixing. The composition is then homogenized with a disperser, e.g., a Gifford-Wood mill, for about 2 minutes. The composition is cooled to 38° C. and the Kathon and perfume are added with mixing for about 10 minutes. The batch is cooled to ambient temperature and stored.

EXAMPLE V

The following is a hair styling conditioner composition which is representative of the present invention.

| Component | Wt. % |
|---|---|
| Disodium EDTA | 0.15 |
| Monosodium Phosphate | 0.04 |
| Disodium Phosphate | 0.12 |
| ADOGEN 470[4] | 0.75 |
| Locust Bean Gum | 0.70 |
| Natrosol Plus CS Grade D-67[1] | 0.70 |
| Glydant | 0.37 |
| Xanthan Gum | 0.25 |
| Perfume | 0.02 |
| Water | q.s. to 100% |
| Silicone Gum Premix | |
| G.E. S E 76[2] | 0.50 |
| Octamethyl Cyclotetrasiloxane | 3.00 |
| Styling Polymer Premix | |
| Styling Polymer[3] | 3.00 |
| Phenyl Pentamethyl Disiloxane | 9.00 |
| Hydroxypropyl Pentamethyl Disiloxane | 6.00 |

[1]Hydrophobically modified hydroxyethylcellulose available from Aqualon
[2]Silicone Gum available from General Electric
[3]Isobutylmethacrylate/2-ethylhexylmethacrylate/N,N-dimethyl-acrylamide copolymer 80/5/15
[4]Partially hydrogenated ditallow dimethyl ammonium chloride, commercially available from Sherex Chemical Company, Dublin, Ohio, USA.

The composition is prepared as follows. The DRO water is heated to 71° C. The ADOGEN 470, disodium EDTA, monosodium phosphate, and disodium phosphate are added and the composition is mixed for about 5 minutes. The silicone gum premix, locust bean gum, and Natrosol are added with mixing. The composition is then homogenized using a disperser, e.g., a Gifford-Wood Mill, for about 2 minutes. The batch is cooled to 38° F. and the Xanthan Gum premix, styling polymer premix, perfume and Glydant are added and mixed for about 10 minutes. The composition is then cooled to ambient temperature and stored.

EXAMPLE VI

The following is a styling rinse composition representative of the present invention.

| Component | Wt. % |
|---|---|
| Styling Agent | |
| Silicone Copolymer[1] | 3.00 |
| Octamethyl cyclotetrasiloxane | 9.00 |
| Premix | |
| Silicone Gum GE SE76[2] | 0.50 |
| Decamethyl cyclopentosiloxane | 4.00 |
| Main Mix | |
| Natrosol Plus CS Grade D-67[3] | 1.25 |
| ADOGEN 470[5] | 0.80 |
| KEMAMINE Q-1902C[6] | 0.40 |
| Kathon CG[4] | 0.03 |
| Imidazole | 0.15 |
| Perfume | 0.10 |
| DRO H$_2$O | q.s. to 100% |

[1]80/20 t-butyacrylate/PDMS macromer, the macromer having a molecular weight of about 10,000, prepared in a manner similar to Example C-2b of U.S. Pat. No. 4,728,571, Clemens issued March 1, 1988.
[2]Commercially available from General Electric
[3]hydrophobically-modified hydroxyethyl cellulose commercially available from Aqualon Co.
[4]preservative commercially available from Rohm & Haas
[5]Partially hydrogenated ditallow dimethyl ammonium chloride, commercially available from Sherex Chemical Company, Dublin, Ohio, USA.
[6]Dimethyl dibehenyl/diarachidyl ammonium chloride, commercially available from Witco Chemical Corporation, Memphis, Tennessee, USA.

The composition is prepared as follows. The Styling Agent and Premix are blended separately by conventional means. The Main Mix is prepared by adding all the ingredients and heating to 95° C. for ½ hour with agitation. As the batch is cooled to about 60° C., the Premix and Styling Agent mixes are added to the Main Mix with agitation and the batch is cooled to ambient temperature.

EXAMPLE VII

The following is a hair styling composition which is representative of the present invention.

| Ingredient | Wt. % |
|---|---|
| Premix 1: | |
| G.E. SE 16 Gum[1] | 0.80 |
| Cab-O-Sil HS-5[2] | 0.20 |
| Decamethylcyclopentasiloxane | 4.50 |
| Premix 2: | |
| G.E. SE 76 Gum | 0.50 |
| Decamethylcyclopentasiloxane | 2.80 |
| Natroso Plus CS Grade D-67[3] | 1.39 |
| Diricinoleyl dimethyl ammonium methyl sulfate (DRDMAMS) | 0.50 |
| Glydant[4] | 0.37 |
| Disodium phosphate | 0.12 |
| Monosodium phosphate | 0.03 |
| Disodium EDTA[5] | 0.15 |
| Fragrance | 0.02 |
| DRO H$_2$O | q.s. to 100% |

[1]Polydimethylsiloxane gum offered by General Electric
[2]Fumed silica offered by the Cabot Corp.
[3]Hydrophobically modified hydroxyethyl cellulose available from Aqualon Co.
[4]Preservative offered by Glyco, Inc.
[5]Ethylene diamine tetraacetic acid The composition is prepared as follows. The DRO water is heated to 65° F. The EDTA, phosphates, and DRDMAMS are added to the water with mixing for about 10 minutes. The Natrosol is then added with mixing for about 5 minutes. The silicone gum premixes are then added with mixing. The composition is then homogenized with a disperser, for example a Gifford-Wood Mill, for about 2 minutes. The batch is cooled to 100° F. The Glydant and perfume are added with mixing for about 10 minutes. The batch is cooled to ambient temperature and stored.

EXAMPLE VIII

The following is a hair conditioner which is representative of the present invention.

| Ingredient | Wt. % |
|---|---|
| Premix: | |
| G.E. SE 76 Gum[1] | 0.10 |
| Decamethylcyclopentasiloxane | 0.60 |
| Natrosol Plus CS Grade D-67[2] | 1.50 |
| Hydrogenated tallowamide DEA | 0.70 |
| Adogen 470[3] | 0.50 |
| Glydant[4] | 0.37 |
| Disodium EDTA[5] | 0.15 |
| Disodium phosphate | 0.12 |
| Monosodium phosphate | 0.03 |
| Fragrance | 0.02 |
| DRO H$_2$O | q.s. to 100% |

[1]Polydimethylsiloxane gum offered by General Electric
[2]Hydrophobically modified hydroxyethyl cellulose available from Aqualon
[3]Di partically(hydrogenated) tallow dimethyl ammonium chloride offered by Sherex Chemical Co.
[4]Preservative offered by Glyco, Inc.
[5]Ethylene diamine tetraacetic acid The composition is prepared as follows. The DRO water is heated to 65° F. The EDTA, phosphates, DEA, and Adogen are added to the water with mixing for about 10 minutes. The Natrosol is then added with mixing for about 5 minutes. The silicone gum premix is then added with mixing. The composition is then homogenized with a disperser, for example a Gifford-Wood Mill, for about 2 minutes. The batch is cooled to 38° F. The Glydant and perfume are added with mixing for about 10 minutes. The batch is cooled to ambient temperature and stored.

EXAMPLE IX

The following is a hair styling rinse composition representative of the present invention.

| Component | Weight % |
|---|---|
| Natrosol Plus CS Grade D-67[1] | 1.15 |
| ADOGEN 470[5] | 0.75 |
| Citric Acid | 0.07 |
| Sodium Citrate | 0.17 |
| Styling Polymer Premix - | |
| Styling Polymer[2] | 2.5 |
| Phenyl Ethyl Pentamethyl Disiloxane | 1.875 |
| Octamethyl Cyclotetrasiloxane | 5.625 |
| Butyl Stearate | 0.20 |
| Silicone Gum Premix - | |
| Polydimethyl Siloxane Gum | 0.35 |
| Decamethyl Cyclopentasiloxane | 1.98 |
| Kathon CG | 0.033 |
| Perfume | 0.2 |
| Xanthan Gum[4] | 0.25 |
| DRO Water | q.s. to 100% |

[1]Hydrophobically modified hydroxyethyl cellulose available from Aqualon Corp.
[2]80/20 t-Butylacrylate/PDMS macromer, the macromer having a molecular weight of about 10,000, prepared in a manner similar to Example C-2b of U.S. Pat. No. 4,728,571, Clemens, issued March 1, 1988
[3]S.E.-76 gum available from General Electric
[4]Readily dispersible xanthan gum
[5]Partially hydrogenated ditallow dimethyl ammonium chloride, commercially available from Sherex Chemical Company, Dublin, Ohio, USA.

The composition is prepared as follows.

The styling polymer premix is prepared by combining the styling polymer, phenyl ethyl pentamethyl disiloxane, butyl stearate, and the octamethyl cyclotetrasiloxane.

The silicone gum premix is prepared by combining, in a separate vessel and mixing the silicone gum and the decamethyl cyclopenta siloxane until homogeneous.

About one-half of the DRO water is first heated to about 66° C. The citric acid, and sodium citrate are added and mixed until homogeneous. The Natrosol and xanthan gum are added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the ADOGEN 470 is added and mixed until homogeneous. The mixture is then cooled to about 43° C. The silicone gum premix is added and the composition homogenized with a homogenizer (in-line preferred).

The two premixes are then combined and mixed until homogeneous to form the styling rinse composition.

EXAMPLE X

The following is a hair styling rinse composition representative of the present invention.

| Component | Weight % |
|---|---|
| Natrosol Plus CS Grade D-67[1] | 1.15 |
| ADOGEN 470[5] | 0.75 |
| Stearyl Alcohol | 0.2 |
| Cetyl Alcohol | 0.3 |
| Citric Acid | 0.07 |
| Sodium Citrate | 0.17 |
| Styling Polymer Premix - | |
| Styling Polymer[2] | 2.5 |
| Decamethyl Cyclopentasiloxane | 1.815 |
| Octamethyl Cyclotetrasiloxane | 5.625 |
| Silicone Gum Premix - | |
| Polydimethyl Siloxane Gum[3] | 0.35 |
| Decamethyl Cyclopentasiloxane | 1.98 |
| Kathon CG | 0.033 |
| Perfume | 0.2 |
| Xanthan Gum[4] | 0.25 |
| DRO Water | q.s. to 100% |

[1]Hydrophobically modified hydroxyethyl cellulose available from Aqualon Corp.
[2]80/20 t-Butyacrylate/PDMS macromer, the macromer having a molecular weight of about 10,000, prepared in a manner similar to Example C-2b of U.S. Pat. No. 4,728,571, Clemens, issued March 1, 1988
[3]S.E.-76 gum available from General Electric
[4]Readily dispersible xanthan gum
[5]Partially hydrogenated ditallow dimethyl ammonium chloride, commercially available from Sherex Chemical Company, Dublin, Ohio, USA.

The composition is prepared as follows.

The styling polymer premix is prepared by combining the styling polymer, decamethyl cyclopentasiloxane, and the octamethyl cyclotetrasiloxane.

The silicone gum premix is prepared by combining, in a separate vessel and mixing the silicone gum and the decamethyl cyclopenta siloxane until homogeneous.

About one-half of the DRO water is first heated to about 66° C. The citric acid, and sodium citrate are added and mixed until homogeneous. The Natrosol and xanthan gum are added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the ADOGEN 470 stearyl alcohol and cetyl alcohol are added and mixed until homogeneous. The mixture is then cooled to about 43° C. The silicone gum premix is added and the composition homogenized with a homogenizer (in-line preferred).

The two premixes are then combined and mixed until homogeneous to form the styling rinse composition.

EXAMPLE XI

The following is a hair styling rinse composition representative of the present invention.

| Component | Weight % |
| --- | --- |
| Natrosol Plus CS Grade D-67[1] | 1.15 |
| ADOGEN 470[5] | 0.75 |
| Citric Acid | 0.07 |
| Sodium Citrate | 0.17 |
| Styling Polymer Premix - | |
| Styling Polymer[2] | 2.5 |
| Phenyl Ethyl Pentamethyl Disiloxane | 1.875 |
| Octamethyl Cyclotetrasiloxane | 5.625 |
| Silicone Gum/Fluid Premix | |
| Polydimethyl Siloxane Gum[3] | 0.20 |
| 350 centistoke Polydimethyl Siloxane Fluid | 0.30 |
| Kathon CG | 0.033 |
| Perfume | 0.2 |
| Xanthan Gum[4] | 0.25 |
| DRO Water | q.s. to 100% |

[1]Hydrophobically modified hydroxyethyl cellulose available from Aqualon Corp.
[2]80/20 t-Butylacrylate/PDMS macromer, the macromer having a molecular weight of about 10,000, prepared in a manner similar to Example C-2b of U.S. Pat. 4,128,571, Clemens, issued March 1, 1988
[3]S.E.-76 gum available from General Electric
[4]Readily dispersible xanthan gum
[5]Partially hydrogenated ditallow dimethyl ammonium chloride, commercially available from Sherex Chemical Company, Dublin, Ohio, USA.

The composition is prepared as follows.

The styling polymer premix is prepared by combining the styling polymer, phenyl ethyl pentamethyl disiloxane, and the octamethyl cyclotetrasiloxane.

The silicone gum/fluid premix is prepared by combining in a separate vessel and mixing the silicone gum and silicone fluid until homogeneous.

About one-half of the DRO water is first heated to about 66° C. The citric acid, and sodium citrate are added and mixed until homogeneous. The Natrosol and xanthan gum are added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the ADOGEN 470 is added and mixed until homogeneous. The mixture is then cooled to about 43° C. The silicone gum/fluid premix is added and the composition homogenized with a homogenizer (in-line preferred).

The two premixes are then combined and mixed until homogeneous to form the styling rinse composition.

EXAMPLE XII

The following is a hair styling rinse composition representative of the present invention.

| Component | Weight % |
| --- | --- |
| Natrosol Plus CS Grade D-67[1] | 1.15 |
| Hydrogenated Tallow Betaine | 0.30 |
| Methyl-1-soya amido ethyl-2-soya imidazolinium (MSAESI) | 0.75 |
| Citric Acid | 0.07 |
| Sodium Citrate | 0.17 |
| Styling Polymer Premix - | |
| Styling Polymer[2] | 2.5 |
| Octamethyl Cyclotetrasiloxane | 5.25 |
| Decamethyl Cyclopentasiloxane | 2.25 |
| Silicone Gum Premix - | |
| Polydimethyl Siloxane Gum[3] | 0.35 |
| Decamethyl Cyclopentasiloxane | 1.98 |
| Kathon CG | 0.033 |
| Perfume | 0.2 |
| Xanthan Gum[4] | 0.25 |
| DRO Water | q.s. to 100% |

[1]Hydrophobically modified hydroxyethyl cellulose available from Aqualon Corp.
[2]80/20 t-Butylacrylate/PDMS macromer, the macromer having a molecular weight of about 10,000, prepared in a manner similar to Example C-2b of U.S. Pat. 4,728,571, Clemens, issued March 1, 1988
[3]S.E.-76 gum available from General Electric
[4]Readily dispersible xanthan gum The composition is prepared as follows.

The styling polymer premix is prepared by combining the styling polymer, the octamethyl tetrasiloxane, and the decamethyl pentasiloxane.

The silicone gum premix is prepared by combining, in a separate vessel and mixing the silicone gum and the decamethyl cyclopentasiloxane until homogeneous.

About one-half of the DRO water is first heated to about 66° C. The hydrogenated tallow betaine, citric acid, and sodium citrate are added and mixed until homogeneous. The Natrosol and xanthan gum are added and mixed until homogeneous. The composition is cooled to about 38° C. The styling polymer premix, Kathon CG and perfume are added. The composition is mixed and homogenized with a homogenizer such as a Tekmar homogenizer (preferably in-line).

The remaining DRO water is heated to about 88° C., the MSAESI is added and mixed until homogeneous. The mixture is then cooled to about 43° C. The silicone gum premix is added and the composition homogenized with a homogenizer (in-line preferred).

The two premixes are then combined and mixed until homogeneous to form the styling rinse composition.

EXAMPLES XIII–XVI

The following are hair styling/conditioning rinse compositions representative of the present invention.

| Composition | XIII | XIV | XV | XVI |
|---|---|---|---|---|
| Citric Acid | 0.02 | 0.02 | 0.02 | 0.02 |
| Sodium Citrate | 0.09 | 0.09 | 0.09 | 0.09 |
| Cetyl Alcohol | 0.12 | 0.12 | 0.12 | 0.12 |
| Stearyl Alcohol | 0.08 | 0.08 | 0.08 | 0.08 |
| Natrosol Plus CS Grade D-67[1] | 1.25 | 1.40 | 0.95 | 1.10 |
| Xanthan Gum[2] | 0.25 | 0.25 | 0.25 | 0.25 |
| Styling Polymer Premix | | | | |
| Styling Polymer[3] | 1.75 | 1.75 | 1.75 | 1.75 |
| Octamethyl Tetrasiloxane | 5.98 | 5.98 | 5.98 | 5.98 |
| Decamethyl Pentasiloxane | 2.56 | 2.56 | 2.56 | 2.56 |
| Butyl Stearate | 0.15 | 0.15 | 0.15 | 0.15 |
| Kathon CG | 0.03 | 0.03 | 0.03 | 0.03 |
| Perfume | 0.33 | 0.33 | 0.33 | 0.33 |
| Thickener Premix | | | | |
| DRO Water | 11.67 | 11.90 | 11.93 | 11.63 |
| Adogen 470[5] | 0.67 | 1.33 | 1.00 | 1.00 |
| Kemamine ® BQ-2802C | 0.33 | — | — | — |
| Stearyl trimethyl ammonium chloride | — | — | 0.30 | — |
| Adogen 471[6] | — | — | — | 0.60 |
| Silicone Gum Premix | | | | |
| Decamethyl Pentasiloxane | 1.98 | 1.42 | 1.42 | 1.42 |
| Polydimethyl Siloxane Gum[4] | 0.35 | 0.25 | 0.25 | 0.25 |
| Amodimethicone (Dow Corning Q2-8220) | — | 0.10 | 0.10 | 0.10 |
| DRO Water | q.s. | q.s. | q.s. | q.s. |

[1]Hydrophobically modified hydroxyethyl cellulose from Aqualon Corp.
[2]Readily dispersible xantham gum
[3]80/20 t-Butylacrylate/PDMS macromer, the macromer having a molecular weight of about 10,000, prepared in a manner similar to Example C-2b of U.S. Pat. 4,728,571, Clemens, issued March 1, 1988.
[4]SE-76 gum available From General Electric
[5]Solution of 75% surfactant and 25% isopropyl alcohol/water for Examples XV and XVI; 100% surfactant for Examples XIII and XIV.
[6]Tallow trimethyl ammonium chloride (Sherex Chemical Co.)

The styling polymer premix is prepared by combining the styling polymer, the octamethyl tetrasiloxane and decamethyl pentasiloxane, and butyl stearate.

The silicone gum premix is prepared by combining and mixing (in a separate vessel) the silicone gum and decamethyl pentasiloxane until homogeneous.

The thickener premix is prepared by combining and mixing (in a separate vessel) DRO water, and any primary and secondary thickeners (premelted if necessary to ensure homogenity) at 82° C., and the silicone gum premix and the amodimethicone at 71° C., until homogeneous.

In another vessel, the DRO water is heated to 71° C. Citric acid, sodium citrate, cetyl alcohol, stearyl alcohol and Natrosol Plus CS grade D-67 are added and mixed until homogeneous. The xanthan gum is added and mixed until homogeneous. The styling polymer premix, Kathon CG and perfume are added and mixed until homogeneous. The composition is further dispersed with an in-line homogenizer (such as Tekmar homogenizer) and then cooled to 38° C.

The thickener premix is also further dispersed with an in-line homogenizer and cooled to 38° C. and added to the final vessel, mixing until homogeneous to form the styling rinse composition.

The compositions hereof comprise or, alternatively, can consist essentially of or consist of the essential ingredients, as well as the various optional ingredients, described herein.

EXAMPLES XVII–XIX

The following are hair styling/conditioning rinse compositions representative of the present invention.

| Composition | I | II | III |
|---|---|---|---|
| Conditioner Premix | | | |
| DRO Water | q.s. | q.s. | q.s. |
| Citric Acid | 0.02 | 0.02 | 0.02 |
| Sodium Citrate | 0.09 | 0.09 | 0.10 |
| Cetyl Alcohol | 0.12 | 0.12 | 0.12 |
| Stearyl Alcohol | 0.08 | 0.08 | 0.08 |
| Natrosol Plus CS Grade D-67[1] | 1.02 | 1.00 | 0.99 |
| Xanthan Gum[2] | 0.25 | 0.25 | 0.25 |
| Styling Polymer Premix | | | |
| Polysiloxane-Grafted Polymer[7] | 1.75 | 1.75 | 1.15 |
| Octamethyl cyclotetrasiloxane | 5.98 | 5.98 | 5.98 |
| Decamethyl cyclopentasiloxane | 2.56 | 2.56 | 2.56 |
| Butyl Stearate | 0.15 | 0.15 | 0.15 |
| Trimethylsiloxysilicate | 0.11 | 0.11 | 0.11 |
| Kathon CG | 0.03 | 0.03 | 0.03 |
| Perfume | 0.33 | 0.33 | 0.33 |
| Silicone Premix | | | |
| DRO Water | 9.48 | 9.48 | 8.57 |
| Adogen 470[4] | 0.70 | 0.60 | 0.93 |
| Adogen 471[5] | 0.05 | 0.15 | 0.07 |
| Decamethyl cyclopentasiloxane/Polydimethyl Siloxane Gum[3] | 1.61 | 1.67 | 2.33 |
| Amodimethicone (Dow Corning Q2-8220)[6] | 0.10 | 0.10 | 0.10 |
| Surfactant Premix | | | |
| DRO Water | 5.70 | 5.70 | 5.70 |
| Stearalkonium Chloride | 0.30 | 0.30 | 0.30 |

[1]Hydrophobically modified hydroxyethyl cellulose from Aqualon Corp.
[2]Readily dispersible xantham gum
[3]SE-76 gum available from General Electric
[4]Ditallow dimethyl ammonium chloride, Sherex Chemical Co., Dublin, Ohio, USA; 75% aqueous solution
[5]Tallow trimethyl ammonium chloride, Sherex Chemical Co.; 50% aqueous solution.
[6]Trimethylsilylamodimethicone
[7]80 wt % t-butyl acrylate/20 wt % silicone macromer(wt average molecular weight of 10,000), polymer weight average molecular weight of about 1,000,000

The styling polymer premix is prepared by combining the polymer, the octamethyl tetrasiloxane and decamethyl pentasiloxane, butyl stearate, and silicone resin.

The silicone premix is prepared by combining and mixing (in a separate vessel) water, Adogen 470 and Adogen 471 at 85° C. Cool to 71° C. and add the silicone gum/decamethyl cyclopentasiloxane solution and Amodimethicone and mix until homogeneous. Cool to 38° C. while using homogenizer (such as Tekmar).

The surfactant premix is prepared by combining and mixing (in a separate vessel) water and Stearalkonium Chloride at 38° C.

The conditioner premix is prepared by combining and mixing (in a separate vessel) the DRO water heated to 71° C. Citric acid, sodium citrate, cetyl alcohol, stearyl alcohol and Natrosol Plus CS grade D-67 are added and mixed until homogeneous. The xanthan gum is added and mixed until homogeneous. The styling polymer premix, Kathon CG and perfume are added and mixed until homogeneous. The composition is further dispersed with an in-line homogenizer (such as Tekmar homogenizer) and then cooled to 38° C.

The conditioner is completed by combining and mixing (in a separate vessel) the conditioner premix, the silicone premix and the surfactant premix at 38° C. This mixture is then cooled to 380° C.

When the compositions defined in Examples I–III are applied to hair in the conventional manner, they provide effective hair conditioning and styling/hold benefits without leaving the hair with a sticky/stiff feel.

What is claimed is:

1. A cosmetic composition useful in application to the hair or skin, comprising:
   (a) from about 80% to about 100% by weight of the composition of a vehicle system which comprises:
      (A) from about 0.1% to about 10.0% by weight of the cosmetic composition of a polymer which comprises a hydrophilic water-soluble polymer backbone having grafted thereto hydrophobic groups selected from the group consisting of $C_8$–$C_{22}$ alkyl, aryl alkyl, alkyl aryl groups and mixtures thereof; wherein the ratio of the hydrophilic backbone to the hydrophobic groups of the polymer is from about 10:1 to about 1000:1;
      (B) from about 0.02% to about 10.0% by weight of the cosmetic composition of unsaturated quaternary ammonium surfactant component of the formula:

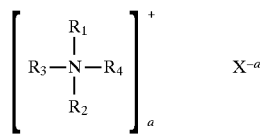

(I)

wherein X is a salt-forming anion, a is the ionic charge of X, the quaternary ammonium radicals $R_1$, $R_2$, $R_3$, and $R_4$ independently are $C_1$–$C_{22}$ alkyl, $C_{14}$–$C_{22}$ alkyl amido $C_2$–$C_6$ alkylene, or benzyl, and from two to three of said quaternary ammonium radicals are $C_{14}$–$C_{22}$ alkyl or $C_{14}$–$C_{22}$ alkyl amido $C_2$–$C_6$ alkylene or mixtures thereof, no more than two of said radicals being $C_{14}$–$C_{22}$ alkyl amido $C_2$–$C_6$ alkylene or a combination of $C_{14}$–$C_{22}$ alkyl and $C_{14}$–$C_{22}$ alkyl amido $C_2$–$C_6$ alkylene, from one to two of said quaternary ammonium radicals are $C_1$–$C_6$ alkyls, and no more than one of said radicals is benzyl; or

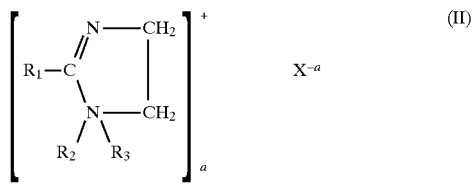

(II)

wherein X is a salt-forming anion, a is the ionic charge of X, radicals $R_1$, $R_2$, and $R_3$ independently are $C_1$–$C_{22}$ alkyl or benzyl, and two or three of said radicals are $C_{14}$–$C_{22}$ alkyl, or $C_{14}$–$C_{22}$ alkyl amido $C_2$–$C_6$ alkylene or a mixture thereof, zero or one of said radicals are $C_1$–$C_6$ alkyl, zero or one of said radicals is benzyl, or a mixture of a Formula I and II surfactants; wherein said quaternary ammonium surfactant component has a level of unsaturation in the $C_{14}$–$C_{22}$ alkyl or $C_{14}$–$C_{22}$ alkyl amido $C_2$–$C_6$ alkylene radicals, or mixture thereof, sufficient to provide the unsaturated quaternary ammonium surfactant component with an average iodine value of at least 15; and
   (C) from about 65% to about 99% by weight of the cosmetic composition of a compatible solvent;
(b) from 0% to about 20%, by weight of the cosmetic composition, of an additional cosmetic component; and
(c) from about 0.05% to about 1.0%, by weight of the cosmetic composition, of a mixture of mono-long chain, tri-short chain quaternary ammonium surfactants of the formula:

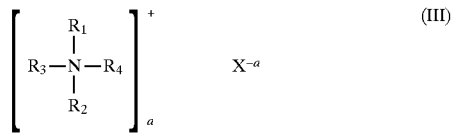

(III)

wherein X is a salt forming anion, a is the ionic charge of X, the quaternary ammonium radical $R_1$ is $C_{14}$–$C_{22}$ alkyl or $C_{14}$–$C_{22}$ alkyl amido $C_2$–$C_6$ alkylene and the quaternary ammonium radicals $R_2$, $R_3$ and $R_4$ independently are $C_1$–$C_6$ alkyl or benzyl, wherein zero or one of said $R_2$, $R_3$, and $R_4$ radicals is benzyl;

wherein said cosmetic composition comprises no more than about 1.0% of water soluble surfactants, and further wherein component (c) is a mixture of (i) $C_{14}$–$C_{22}$ alkyl, $C_1$–$C_3$ dialkyl, benzyl ammonium salts, and (ii) unsaturated $C_{14}$–$C_{22}$, tri $C_1$–$C_3$ alkyl ammonium salts, and the ratio of (i):(ii) is from about 0.5:1 to about 8:1.

2. The composition of claim 1, wherein said radicals of Formula I are selected from the group consisting of $C_{14}$–$C_{22}$ alkyl, $C_1$–$C_6$ alkyl, benzyl, and $C_{14}$–$C_{22}$ alkyl amido $C_2$–$C_6$ alkylene, and said radicals of Formula II are selected from the group consisting of $C_{14}$–$C_{22}$ alkyl, $C_1$–$C_6$ alkyl, benzyl, and $C_{14}$–$C_{22}$ alkyl amido $C_2$–$C_6$ alkylene.

3. The composition of claim 2, wherein the unsaturated quaternary ammonium surfactant is selected from the group consisting of compounds of Formula I wherein two of said radicals are $C_{16}$–$C_{22}$ alkyl, from one to two of said radicals are $C_1$–$C_3$ alkyl, and zero or one of said radicals is benzyl, and compounds of Formula II wherein two of said radicals are $C_{16}$–$C_{22}$ alkyl, and one of said radicals is $C_1$–$C_3$ alkyl or benzyl.

4. The composition of claim 3, wherein said unsaturated quaternary ammonium surfactant component is selected from Formula I and comprises from one to two methyl radicals, zero or one benzyl radical, and two $C_{16}$–$C_{18}$ alkyls.

5. The composition of claim 1, wherein said unsaturated quaternary ammonium surfactant comprises a salt of dimethyl di(unsaturated) tallow ammonium, dimethyl di(unsaturated)arachidyl ammonium, dioleyl dimethylammonium, di-rapeseed alkyl dimethyl ammonium, diricinoleyl dimethyl ammonium, disoyadimonium, olealkonium, methyl-1-oleyl amido ethyl-2-oleyl imidazolinium, dierucyl dimethyl ammonium, or methyl-1-soya amido ethyl-2-soya imidazolinium.

6. The composition of claim 1 wherein said polymer (A) comprises a nonionic cellulose ether having nonionic substitution selected from the group consisting of methyl, hydroxyethyl, and hydroxypropyl, in an amount sufficient to cause the cellulose ether to be water-soluble and being further substituted with a long chain alkyl radical having 10 to 24 carbon atoms in an amount between about 0.2 weight percent and the amount which renders said polymer (A) less than 0.2% by weight soluble in water.

7. The composition of claim 6 wherein the vehicle system provides a rheology to the cosmetic composition that is characterized by a shear stress of from 0 to about 50 pascal over a shear rate range of from about 0.04 $\sec^{-1}$ to about 25 $\sec^{-1}$.

8. The composition of claim 7 wherein the long-chain alkyl radical is attached to the cellulose ether via an ether linkage.

9. The composition of claim 8 wherein the polymer (A) comprises a water-soluble hydroxypropyl cellulose substituted with a long-chain alkyl radical having 10 to 24 carbon atoms in an amount between about 0.2 weight percent and the amount which renders the polymer (A) less than 1% by weight soluble in water.

10. The composition of claim 9 wherein the hydroxyethyl cellulose prior to substitution with the long chain alkyl group has a molecular weight of about 50,000 to 700,000.

11. The composition of claim 10 wherein the water-soluble hydroxyethyl cellulose is substituted with a long chain alkyl radical having about 16 carbon atoms in an amount between about 0.40% to about 0.95%, by weight; the hydroxyethyl molar substitution is from about 2.3 to about 3.7; and the average molecular weight of the unsubstituted cellulose is from about 300,000 to about 700,000.

12. The composition of claim 3 which comprises from about 0.05% to about 3.0%. of said unsaturated quaternary ammonium surfactant component.

13. The composition of claim 6, wherein said radicals of Formula I are selected from the group consisting of $C_{14}$–$C_{22}$ alkyls, $C_1$–$C_6$ alkyls, benzyl, and $C_{14}$–$C_{22}$ alkyl amido $C_2$–$C_6$ alkylene, and said radicals of Formula II are selected from the group consisting of $C_{14}$–$C_{22}$ alkyls, $C_1$–$C_6$ alkyls, benzyl, and $C_{14}$–$C_{22}$ alkyl amido $C_2$–$C_6$ alkylene.

14. The composition of claim 13, wherein the unsaturated quaternary ammonium surfactant is selected from the group consisting of compounds of Formula I wherein two of said radicals are $C_{16}$–$C_{22}$ alkyls, from one to two of said radicals are $C_1$–$C_3$ alkyls, and zero or one of said radicals is benzyl and compounds of Formula II wherein two of said radicals are $C_{16}$–$C_{22}$ alkyls, and one of said radicals is $C_1$–$C_3$ alkyl or benzyl.

15. The composition of claim 14, wherein said surfactants of Formula I comprises from one to two methyl radicals and zero or one benzyl radical.

16. The composition of claim 1 wherein the composition comprises no more than about 1% of fatty alcohol materials.

17. The cosmetic composition of claim 1 which is a hair care composition comprising at least about 0.1% of the additional active cosmetic component and wherein said additional cosmetic component comprises a hair conditioning component selected from the group consisting of a volatile silicone fluid having a viscosity of less than about 10 centipoise at 25° C.; a non-volatile silicone fluid having a viscosity of less than about 100,000 centipoise at 25° C.; a silicone gum having a viscosity greater than about 1,000,000 centipoise at 25° C.; and mixtures thereof.

18. The cosmetic composition of claim 1 wherein said additional cosmetic component comprises a hair styling polymer present in said composition at a level of about 0.1%, by weight.

19. A composition according to claim 1 which further comprises as the additional cosmetic component a hair styling/conditioning agent at a level of 0.1% to about 10% of said composition.

20. A hair care composition according to claim 17 which further comprises as an active cosmetic component a hair styling/conditioning agent at a level of 0.1% to about 10% of said composition.

21. The composition of claim 19 wherein the hair styling/conditioning agent comprises a copolymer comprising C monomers and components selected from the group consisting of A monomers, B monomers, and mixtures thereof, wherein:

A is at least one free radically polymerizable monomer, the amount by weight of A monomer, when used, being up to about 98% by weight of the total weight of all monomers in said copolymer;

B is at least one monomer copolymerizable with A, the amount by weight of B monomer, when used, being up to about 98% of the total weight of all monomers in said copolymer, said B monomer being selected from monomers that are polar relative to A; and C is a polymeric monomer having a molecular weight of from about 1,000 to about 50,000 and of the general formula $X(Y)_n Si(R)_{3-m}(Z)_m$, wherein X is a vinyl group copolymerizable with the A and B monomers, Y is a divalent linking group, R is a hydrogen, lower alkyl, aryl or alkoxy, Z is a polymeric moiety having a number average molecular weight of at least about 500, is pendant from said vinyl polymeric backbone after polymerization, and is of the formula

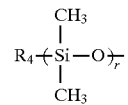

wherein $R^4$ is alkyl, alkoxy, alkylamino, aryl or hydroxyl, and r is an integer of from about 5 to about 700, n is 0 or 1, and m is an integer from 1 to 3, wherein C comprises from about 0.01% to about 50% of the copolymer.

22. The composition of claim 21 wherein the copolymer comprises from about 5% to about 98% A monomer, from about 0.1% to about 50% C monomer, and from 0% to about 98% B monomer.

23. The composition of claim 19 wherein the hair styling/conditioning agent comprises a lipophilic low polarity free radically polymerizable vinyl monomer (A), a hydrophilic polar monomer (B) which is copolymerizable with monomer (A), and a silicone macromer having a weight average molecular weight of from about 1,000 to about 50,000 based on polydimethylsiloxane of the formula:

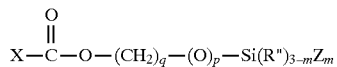

wherein m is 1, 2 or 3; p is 0 or 1; R" is alkyl or hydrogen; q is an integer from 2 to 6; X is

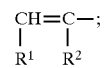

$R^1$ is hydrogen or —COOH; $R^2$ is hydrogen, methyl or —CH$_2$COOH; Z is

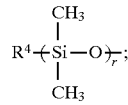

$R^4$ is alkyl, alkoxy, alkylamino, aryl, or hydroxyl; and r is an integer from about 5 to about 700.

24. A hair care composition according to claim 23 wherein monomer A is selected from the group consisting of acrylic acid esters of $C_1$–$C_{18}$ alcohols, methacrylic acid esters of $C_1$–$C_{18}$ alcohols, styrene, vinyl acetate, vinyl chloride, vinylidene chloride, acrylonitrile, alpha-methylstyrene, t-butylstyrene, butadiene, cyclohexadiene, ethylene, propylene, vinyl toluene, polystyrene macromer, and mixtures thereof.

25. A hair care composition according to claim 24 wherein monomer B is selected from the group consisting of acrylic acid, methacrylic acid, N,N-dimethylacrylamide, dimethylaminoethyl methacrylate, quaternized dimethylaminoethyl methacrylate, methacrylonitrile, methacryloamide, maleic anhydride, itaconic acid, acrylamide, hydroxyethyl methacrylate, diallyldimethyl ammonium chloride, vinyl pyrrolidone, maleimides, vinyl pyridine, vinyl imidazole, styrene sulfonate, and mixtures thereof.

26. A hair care composition according to claim 25 wherein monomer A is selected from the group consisting of n-butylmethacrylate, isobutylmethacrylate, 2-ethylhexyl methacrylate, t-butylacrylate, t-butylmethacrylate, methylmethacrylate, and mixtures thereof.

27. A hair care composition as in claim 1, wherein the weight ratio of the total of the surfactants of Formula I and Formula II to Formula III is from about 1:1 to about 4:1.

28. The composition of claim 27, wherein said radicals of Formula I are selected from the group consisting of $C_{14}$–$C_{22}$ alkyls, $C_1$–$C_6$ alkyls, benzyl, and $C_{14}$–$C_{22}$ alkyl amido $C_2$–$C_6$ alkylene, and said radicals of Formula II are selected from the group consisting of $C_{14}$–$C_{22}$ alkyls, $C_1$–$C_6$ alkyls, benzyl, and $C_{14}$–$C_{22}$ alkyl amido $C_2$–$C_6$ alkylene.

29. The composition of claim 28, wherein the unsaturated quaternary ammonium surfactant is selected from the group consisting of compounds of Formula I wherein two of said radicals are $C_{16}$–$C_{22}$ alkyls, from one to two of said radicals are $C_1$–$C_3$ alkyls, and zero or one of said radicals is benzyl, and compounds of Formula II wherein two of said radicals are $C_{16}$–$C_{22}$ alkyls, and one of said radicals is $C_1$–$C_3$ alkyl or benzyl.

30. The composition of claim 29, wherein said unsaturated quaternary ammonium surfactant component is selected from Formula I and comprises from one to two methyl radicals, zero or one benzyl radical, and two $C_{16}$–$C_{18}$ alkyls.

31. The composition of claim 1, wherein component (c)(i) is one or more $C_{16}$–$C_{18}$ alkyl dimethyl benzyl ammonium salts, component (c)(ii) is one or more unsaturated $C_{16}$–$C_{18}$ alkyl trimethyl ammonium salts, and the weight ratio of (c)(i):(c)(ii) is from about 1:1 to about 5:1.

32. The composition of claim 31, wherein the components (c)(i) and (c)(ii) are chloride salts and the weight ratio of (c)(i):(c)(ii) is from about 1.5:1 to about 4:1.

* * * * *